US010436682B2

(12) United States Patent
Bartko et al.

(10) Patent No.: US 10,436,682 B2
(45) Date of Patent: Oct. 8, 2019

(54) SAMPLE PREPARATION FOR SPECTROSCOPY ANALYSIS

(71) Applicant: Battelle Memorial Institute, Columbus, OH (US)

(72) Inventors: Andrew P. Bartko, Columbus, OH (US); Theodore J. Ronningen, Lewis Center, OH (US)

(73) Assignee: BATTELLE MEMORIAL INSTITUTE, Columbus, OH (US)

( * ) Notice: Subject to any disclaimer, the term of this patent is extended or adjusted under 35 U.S.C. 154(b) by 451 days.

(21) Appl. No.: 15/168,070

(22) Filed: May 29, 2016

(65) Prior Publication Data
US 2016/0274101 A1 Sep. 22, 2016

Related U.S. Application Data

(63) Continuation-in-part of application No. 14/689,159, filed on Apr. 17, 2015, now Pat. No. 9,354,146, (Continued)

(51) Int. Cl.
| | |
|---|---|
| *G01N 1/30* | (2006.01) |
| *C12M 1/12* | (2006.01) |
| *C12M 1/34* | (2006.01) |
| *G01N 1/31* | (2006.01) |
| *G01N 1/22* | (2006.01) |

(Continued)

(52) U.S. Cl.
CPC ............ *G01N 1/30* (2013.01); *C12M 25/00* (2013.01); *C12M 41/46* (2013.01); *G01N 1/2202* (2013.01); *G01N 1/312* (2013.01); *B82Y 15/00* (2013.01); *G01N 2001/2223* (2013.01);

(Continued)

(58) Field of Classification Search
CPC ....................................................... G01N 1/00
See application file for complete search history.

(56) References Cited

U.S. PATENT DOCUMENTS

| | | | |
|---|---|---|---|
| 3,574,064 A | 4/1971 | Binnings et al. | |
| 5,776,748 A * | 7/1998 | Singhvi ............... | B01J 19/0046 435/174 |
| 5,866,430 A * | 2/1999 | Grow .................... | G01N 21/65 436/172 |
| 6,544,798 B1 | 4/2003 | Christensen et al. | |

(Continued)

FOREIGN PATENT DOCUMENTS

| | | |
|---|---|---|
| AU | 2006202931 A1 | 8/2006 |
| WO | 01/57254 A2 | 8/2001 |

OTHER PUBLICATIONS

Notification Concerning Transmittal of International Preliminary Report on Patentability and Written Opinion of the International Searching Authority for PCT Application No. PCT/US2011/026959; dated Sep. 13, 2012; The International Bureau of WIPO; Geneva, Switzerland and European Patent Office; Rijswijk, Netherlands.

(Continued)

*Primary Examiner* — Jyoti Nagpaul
(74) *Attorney, Agent, or Firm* — Thomas E. Lees, LLC

(57) ABSTRACT

A Raman silent substrate includes a base and a biologically compatible material layer over the base. The biologically compatible material layer is Raman silent, provides a predetermined capture efficiency corresponding to a desired application, and supports biological culturing. In certain implementations, the base comprises a glass layer and an aluminum layer between the glass layer and the biologically compatible material layer.

20 Claims, 19 Drawing Sheets

Related U.S. Application Data which is a continuation of application No. 13/597,418, filed on Aug. 29, 2012, now Pat. No. 9,034,278, which is a continuation of application No. PCT/US2011/026959, filed on Mar. 3, 2011.

(60) Provisional application No. 61/310,071, filed on Mar. 3, 2010.

(51) Int. Cl.
  *G01N 35/00*    (2006.01)
  *G01N 35/04*    (2006.01)
  *B82Y 15/00*    (2011.01)

(52) U.S. Cl.
  CPC .............. *G01N 2035/00356* (2013.01); *G01N 2035/0441* (2013.01); *Y10T 436/2575* (2015.01)

(56) References Cited

U.S. PATENT DOCUMENTS

| | | |
|---|---|---|
| 2003/0032191 A1 | 2/2003 | Hilson et al. |
| 2003/0082605 A1 | 5/2003 | Hodge |
| 2006/0105359 A1 | 5/2006 | Favuzzi et al. |
| 2008/0145891 A1 | 6/2008 | Burton |

OTHER PUBLICATIONS

International Search Report and the Written Opinion of the International Searching Authority for PCT Application No. PCT/US2011/026959; dated Aug. 4, 2011; European Patent Office; Rijswijk, Netherlands.

European Examination Report for European Patent Application No. 11708637.1; European Patent Office; Munich, Germany; dated Jul. 24, 2018.

\* cited by examiner

SAMPLE PREPARATION FOR SPECTROSCOPY ANALYSIS

CROSS-REFERENCE TO RELATED APPLICATIONS

This application is a continuation-in-part of U.S. patent application Ser. No. 14/689,159, filed Apr. 17, 2015, entitled "SAMPLE PREPARATION FOR SPECTROSCOPY ANALYSIS", now allowed, which is a continuation of U.S. patent application Ser. No. 13/597,418, filed Aug. 29, 2012, entitled "SAMPLE PREPARATION FOR SPECTROSCOPY ANALYSIS", now issued as U.S. Pat. No. 9,034,278, which is a continuation of International Application No. PCT/US2011/026959, filed Mar. 3, 2011, entitled "SAMPLE PREPARATION FOR SPECTROSCOPY ANALYSIS", which claims the benefit of U.S. Provisional Patent Application Ser. No. 61/310,071, filed Mar. 3, 2010, entitled "SAMPLE PREPARATION FOR SPECTROSCOPY ANALYSIS", the disclosures of which are hereby incorporated by reference.

BACKGROUND

The present disclosure relates in general to systems and methods for sample preparation, including sample clean-up and/or purification of samples in preparation for spectroscopy analysis. The present disclosure further relates to systems and methods for increasing the collection efficiency of impacted biological aerosols.

The monitoring of particulate matter has received an increasing amount of attention in recent years because of the potential impact of particulates on radiative and climatic processes, on contamination of products, on human health and because of the role particles play in atmospheric transport and deposition of pollutants. As an illustration, it may be desirable to detect the presence of particulates in the air, in water supplies or on persons. It may also be desirable to detect the presence of particulates on materials that may be found in semiconductor clean rooms, pharmaceutical production facilities and biotechnology laboratories to verify that there has been no contamination produced in such environments that would create undesirable environmental exposures or adversely affect manufacturing, testing or experimental processes.

As another illustration, it may be desirable to analyze the air in a predetermined location for particulates that fall within a range of sizes that can be inhaled, such as naturally occurring or artificially produced airborne pathogens, allergens, bacteria, viruses, fungi and biological or chemical agents that are found in or are otherwise introduced into the location. For example, the ability to detect the presence of particular airborne particulates in hospitals, nursing homes, rehabilitation centers and other care facilities may be beneficial to assist in preventing the spread of disease, infection or harmful bacteria.

The monitoring of particulate matter further finds application for assessments of human health risk, environmental contamination and for compliance with National Ambient Air Quality Standards (NAAQS), e.g., to monitor the air in public and commercial building air clean-up and distribution systems, work sites such as mines, sewage facilities, agricultural and manufacturing facilities, outside areas such as street corners, flues and smokestacks and other locations where it is desirable to monitor environmental hygiene.

BRIEF SUMMARY

According to aspects of the present disclosure, a Raman silent substrate comprises a base and a biologically compatible material layer over the base. The biologically compatible material layer is Raman silent, provides a predetermined capture efficiency corresponding to a desired application, and supports biological culturing. More particularly, the biologically compatible material layer is Raman silent to the extent that the Raman silent substrate does not contribute to a Raman signature collected during a spectroscopic evaluation of a biological target collected upon the Raman silent substrate. Also, the biologically compatible material layer provides a predetermined capture efficiency of the Raman signature collected during the spectroscopic evaluation, and supports biological culturing of the biological target collected upon the substrate.

In an example implementation, the base comprises a glass layer, and an aluminum layer between the glass layer and the biologically compatible material layer.

According to further aspects of the present disclosure, a Raman silent substrate comprises a base and a biologically compatible material layer over the base. The biologically compatible material layer is Raman silent to the extent that the Raman silent substrate does not contribute to a Raman signature collected during a spectroscopic evaluation of a biological target collected upon the Raman silent substrate. Also, the biologically compatible material layer provides a predetermined capture efficiency of the Raman signature collected during the spectroscopic evaluation, and supports biological culturing of the biological target collected upon the substrate. Still further, the biologically compatible material layer includes a thickness less than a wavelength of light divided by two times a numerical aperture of collection optics of a corresponding spectroscopic system. Still further, the biologically compatible material layer is free of symmetrical molecular moieties and is further free of unsaturated chemical bonds. Yet further, the biologically compatible material layer includes a hydrophobic material corresponding to a hydrophobicity of the biological target.

According to yet further aspects of the present disclosure, a Raman silent substrate comprises a base and a biologically compatible material layer over the base. The biologically compatible material layer is Raman silent to the extent that the Raman silent substrate does not contribute to a Raman signature collected during a spectroscopic evaluation of a biological target collected upon the Raman silent substrate. Also, the biologically compatible material layer provides a predetermined capture efficiency of the Raman signature collected during the spectroscopic evaluation, and supports biological culturing of the biological target collected upon the substrate. Still further, the biologically compatible material layer is free of symmetrical molecular moieties and is further free of unsaturated chemical bonds. Yet further, the biologically compatible material layer includes a hydrophilic material that is a non-selective binding material that promotes adhesion. Still further, the biologically compatible material layer is less than 150 nanometers in thickness.

BRIEF DESCRIPTION OF THE SEVERAL VIEWS OF THE DRAWINGS

The following detailed description of various aspects of the present disclosure can be best understood when read in conjunction with the following drawings, where like structure is indicated with like reference numerals, and in which.

DETAILED DESCRIPTION

Figure 1:
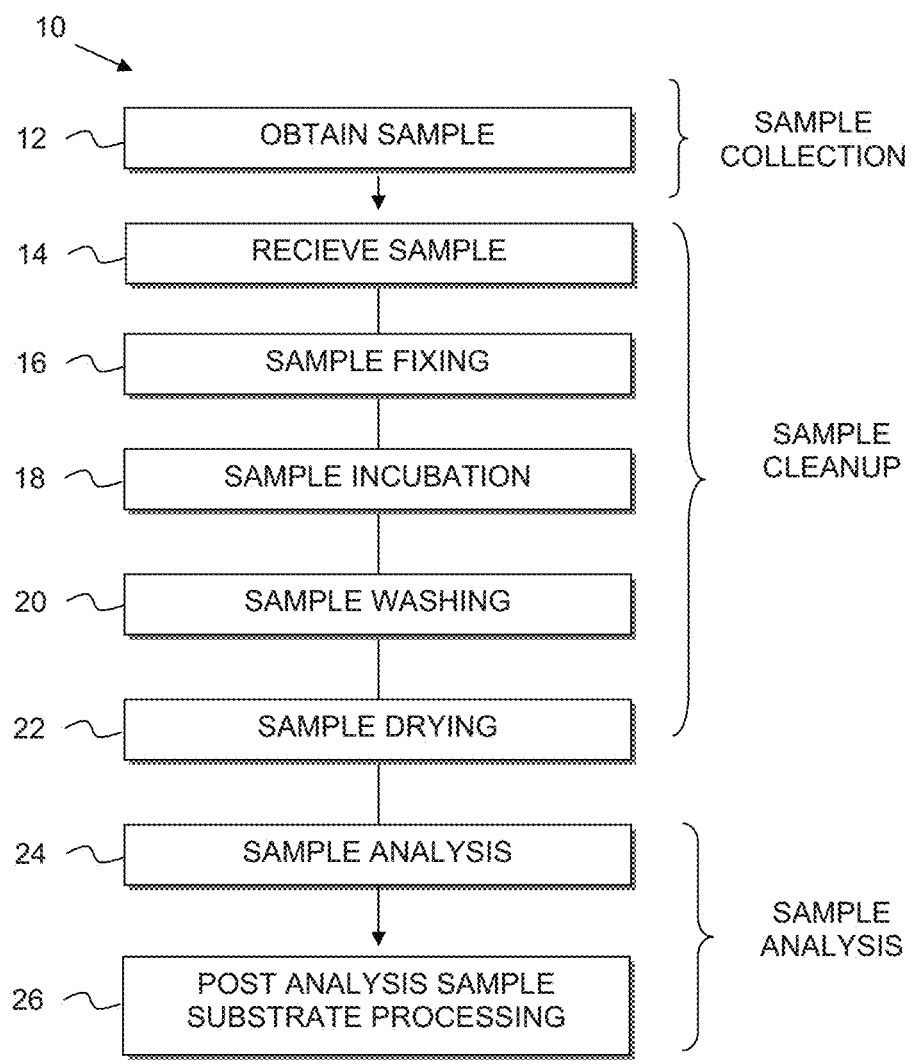
FIG. 1 is a flow chart illustrating a method and process that includes preparing a sample for spectroscopy analysis according to various aspects of the present disclosure.

Currently, biological samples that have been collected from aerosol samplers, biological culture and reagent samples, infectious samples from patients, and other mixed samples, often contain impurities that impede an associated analytical process. Particularly, such impurities can create high interference noise that may mask the spectral signature of a biological specimen of interest in a given spectra generated as part of the associated analytical process. For example, in the spectrographic detection of microbial cells and spores, inorganic compounds such as ammonium sulfate and organic compounds that are commonly found in ambient aerosol samples or biological culture and reagent samples are often found in concentrations on the substrate surface that are high enough to obscure the specimen from microscopic detection. Correspondingly, the concentration of one or more impurities may mask the spectral signature of a biological agent within a sample thereby providing a false negative because the intensity of the impurity peak dominates the spectrogram.

According to various aspects of the present disclosure, systems and methods are provided to prepare a sample for spectroscopy analysis, such as Raman, infrared, fluorescence, mass spectroscopy, etc. The sample preparation, which includes sample clean-up, eliminates or otherwise reduces the high interference noise caused by impurities in a sample under analysis. Such sample preparation facilitates and enhances both spectroscopic targeting and identification of microorganism cells and spores that may be present in a mixed sample, e.g., in an aerosol (bioaerosol) sample, an aqueous sample, as protein particles in an aerosol sample, etc., as will be described in greater detail herein. Thus, in an exemplary implementation, a sample substrate can be cleaned and/or purified in such a way that the substrate retains vegetative bacterial cells, bacterial spores, protein aerosol particles, etc., that are of interest, while removing or reducing contaminants or other impurities.

According to various aspects of the present disclosure, processes are also provided that retain or fix biological particles, e.g., cells, spores, and protein particles, on a slide substrate while removing interferant particles from the substrate. Interferant particles may include for example, salts, medium components, and other impurities. Accordingly, the "cleaned-up" samples can be directly presented to an assay under an analytical and detection instrument, such as a Raman spectroscopy, Infrared spectroscopy, a fluorescence spectroscopy, a mass spectroscopy, etc. Still further, as will be described in greater detail herein, various aspects of the present disclosure can be integrated into various analytical or diagnostic processes of sample targeting and identification thus providing utility for sample analyses, for example, in environmental, biotechnological, forensic, and medical diagnostic areas.

Referring now to the drawings, and in particular, to FIG. 1, a process 10 is illustrated, which includes components for sample collection, sample clean-up and sample analysis, according to various aspects of the present disclosure. The sample collection portion of the process 10 includes obtaining a sample at 12 on a sample substrate such as a slide. The sample can be obtained by collecting the sample from the air, collecting the sample from a water supply or other source of liquid, collecting the sample from a sample dispenser, or otherwise obtaining the sample on a slide substrate. Thus, the sample can be an aerosol sample, liquid sample, environmental sample, e.g., a material, component, product, etc. Examples of obtaining a sample are set out in greater detail herein.

The sample clean-up portion of the process 10 optionally includes receiving a slide substrate having a sample thereon at 14. For instance, depending upon the technology utilized to obtain the sample at 10, it may be necessary to relocate a previously obtained sample to a clean-up device, area, station, etc. The sample clean-up portion of the process also comprises fixing the sample to the sample substrate at 16. In exemplary implementations, the sample is fixed by optionally applying a fixing solution to the sample on the slide substrate and by heating the sample for a predetermined heating time, e.g., at a controlled temperature. After fixing the sample to the sample substrate, the sample clean-up portion of the process 10 includes incubating the sample at 18. In exemplary implementations, the sample is incubated by optionally applying an incubation solution to the sample on the slide substrate and holding the sample for a predetermined incubation time.

After incubation, the sample clean-up portion of the process 10 includes washing the sample at 20. In exemplary implementations, the sample is washed by applying a washing solution to the sample on the slide substrate for a predetermined washing time. After washing, the sample clean-up portion of the process 10 includes drying the sample at 22. In exemplary implementations, the sample is dried by heating the sample for a predetermined drying time.

The sample is thus prepared for subsequent sample analysis at 24 during the sample analysis portion of the process 10, which includes for instance, spectroscopy analysis such as a Raman spectroscopy, Infrared spectroscopy, a fluorescence spectroscopy, a mass spectroscopy, or any combination thereof. Upon completion of the analysis at 24, desired post analysis sample substrate processing is implemented at 26. In exemplary implementations, the sample substrate is relocated to a sample substrate storage, or the sample substrate may be discharged to a discharge area, e.g., for disposal or cleaning for re-use, etc.

Sample Processing System

Referring to FIG. 2, a sample processing is schematically illustrated, which can be utilized, for example, to implement the process 10 of FIG. 1. The sample processing system 50 is comprised of a plurality of "stations" where each station is utilized to perform an aspect of the process 10 of FIG. 1. In the illustrative example, there are seven stations, including a sample deposition station 52, a sample fixing station 54, a sample incubation station 56, a sample washing station 58, a sample drying station 60, a sample analysis station 62 and a sample disposition station 64.

The sample deposition station 52 is utilized to obtain a sample, collected onto a sample substrate. In illustrative implementations, the sample deposition station 52 includes a sample collection device 72 that is utilized to collect or otherwise deposit a sample 74 onto a sample substrate. For purposes of illustration, the sample substrate is implemented as a slide substrate 76.

In exemplary implementations, the sample collection device 72 comprises an aerosol collection device. Examples of a suitable aerosol sample collection device include an impactor, such as a solid surface small area impactor, a virtual impactor, a cascade impactor, an electrostatic precipitation device, a cyclone device, or other device that can be used to remove particulates including bioaerosol particles from the air and deposit the collected particulates into a small area on the slide substrate 76. In exemplary implementations, the sample collection device 72 is implemented as an aerosol collector that draws and accelerates a fluid stream, such as from the ambient air, through a collection component. Particulate matter that is entrained in the stream is extracted and deposited onto the slide substrate 76, e.g., in a relatively small, defined sample area.

The use of an aerosol collection device is utilized, for instance, in an exemplary application where the system 50 is configured to sample the air for particulates that fall within a range of sizes that can be inhaled. In exemplary implementations, the system 50 is used to discriminate nitrate and sulfate, ammonium, fungal spores and other particulates in collected samples. As such, the sample collection device 72 within the sample deposition station 52 may be designed to collect and deposit particulates generally within the size range of approximately 1 µm to 10 µm on the slide substrate 76.

However, in alternative exemplary implementations, the sample deposition station 52 collects other types of environmental samples, including samples of different sizes. Moreover, the sample collection device 72 can be used to collect samples from different sources other than ambient aerosols. For instance, in exemplary implementations, the sample collection device 72 comprises a sample dispenser such as a micro liter liquid sample dispenser. Still further, in exemplary implementations, the sample collection device 72 is a device that facilitates the collection of a sample, such as from a material, component, product, etc., in a manufacturing or testing process, from a pharmaceutical, or other environment, onto the slide substrate 76. In still further exemplary implementations, the sample collection device 72 is a device that facilitates the collection of a sample from a water supply, or from other sources, onto the slide substrate 76, e.g., to test for contamination or other characteristics of interest.

Depending upon the specific implementation of the collection technology, the sample deposition station 52 can contain any other components necessary to implement sample collection and/or deposition, such as necessary pumps, power supplies, stains, etc.

The slide substrate 76 comprises is a substrate suitable for collecting the sample. For example, in exemplary implementations, the slide substrate 76 comprises a solid surface or other configuration suitable for collecting a sample thereon. In other exemplary implementations, the slide substrate 76 comprises a non-Raman active membrane filter material or other form of filter material.

The collected sample 72 contains the particles of analytical interests, which may include for example, microorganism cells (e.g. bacteria or yeast), spores and protein particles, as described in greater detail herein. The collected sample 72 may also contain impurities such as salts and other compounds that can interfere with the successful identification of the analytical(s) of interest.

In an automated implementation of the system 50, an instance of a slide substrate 76 is fed and positioned at the sample deposition station 52 by an automatic actuator or other automated stage (e.g., linear translation stage, rotary stage, or other automated translation system or subsystem). The slide substrate 76 can alternatively be manually placed in the sample deposition station 52 prior to initiation of a sample collection operation.

After a suitable sample 74 has been collected onto a corresponding slide substrate 76, the slide substrate 76 is delivered to the sample fixing station 54. In exemplary implementations, the delivery of the slide substrate 76 to the sample fixing station 54 is implemented by a sample slide feeder, e.g., an automatic delivery mechanism such as a translation stage that automates movement of the slide substrate 76 between the sample collection station 52 and the sample fixing station 54.

Any number of suitable triggers can be utilized to determine when a slide substrate 76 staged at the sample collection station 52 should be transitioned to the sample fixing station 54. As a few illustrative examples, the sample collection process can be time synchronized or otherwise time limited. As an alternative example, the time that a particular slide substrate 76 spends at the sample deposition station 52 can be dependent upon the amount of time required to achieve a predetermined buildup of particulates on the corresponding slide substrate 76. Still further, initiation of the sample collection process at the sample deposition station 52 can be automatically triggered, e.g., via the detection of a slide substrate 76 positioned in register with the sample collection device 72. Alternatively, the sample collection process can be manually initiated, e.g., via operator actuation of a corresponding control feature of the system 50.

After positioning the substrate 76 at the sample fixing station 54, a sample fixing operation is performed. In exemplary implementations, during a sample fixing process, a sample prefixing solution is added to the sample 74 on the slide substrate 76. For example, as illustrated, a dispenser 80 is utilized to eject the prefixing solution, which can comprise pure deionized water or a mixed solution containing alcohols such as ethanol, over the sample 74. Other organic solvents can also be added to the prefixing solution, e.g., depending on the sample nature and purification requirements. In this regard, in exemplary implementations, the dispenser 80 is positioned at the sample fixing station 54. In other exemplary implementations, the dispenser 80 dispenses the prefixing solution on the sample 74 at some point before the sample is fixed at the sample fixing station 54, e.g., while the corresponding slide substrate 76 is traveling to the sample fixing station 54.

After the sample 74 has been suitably treated with a prefixing solution, the sample 74 is fixed, e.g., for 5-60 seconds. Fixing can be accomplished by heating the sample 74. In exemplary implementations, the slide substrate 76 is transitioned onto a heated surface 82, which is heated to a controlled temperature. The controlled temperature ranges by way of illustration, from approximately 65° Celsius (C) to 115° C.

After fixing, the sample 74 on the slide substrate 76 is automatically transferred to the sample incubation station 56. In exemplary implementations, during a sample incubation process, an incubation solution is added to cover the entire sample area of the sample 74 on the slide substrate 76. For example, in exemplary implementations, the dispenser 80 is utilized to eject the incubation solution, which can comprise pure deionized water, a mixed solution containing alcohols such as ethanol, or other organic solvents, over the sample 74. In exemplary implementations, the dispenser 80 is positioned at the sample incubation station 56. In other exemplary implementations, the dispenser 80 dispenses the incubation solution on the sample 74 at some point before the sample is incubated at the sample incubation station 56, e.g., while the corresponding slide substrate 76 is traveling to the sample incubation station 56. The incubation time at the sample incubation station 56 can range for example, from approximately 5 seconds to approximately 60 seconds. However, longer incubation times can be utilized, e.g., depending upon the nature of the collected sample 74.

At the completion of incubation, the slide substrate 76 is further automatically transported to the sample washing station 58, where the sample is washed with a washing solution. In a manner analogous to that set out above, during a washing process, a wash solution is applied to the sample area of the sample 74 on the slide substrate 76. The washing solution can be deionized water, a mixed solution containing alcohols such as ethanol, a solvent solution, or a solution added with selected chemical(s) to enhance the sample clean-up process. For example, the dispenser 80 can be utilized to eject the wash solution over the sample 74. In analogous fashion to that described above, in exemplary implementations, the dispenser 80 is positioned at the sample washing station 58. In alternative exemplary implementations, the dispenser 80 dispenses the wash solution on the sample 74 at some point before the sample fully reaches the sample washing station 58.

Figure 2:
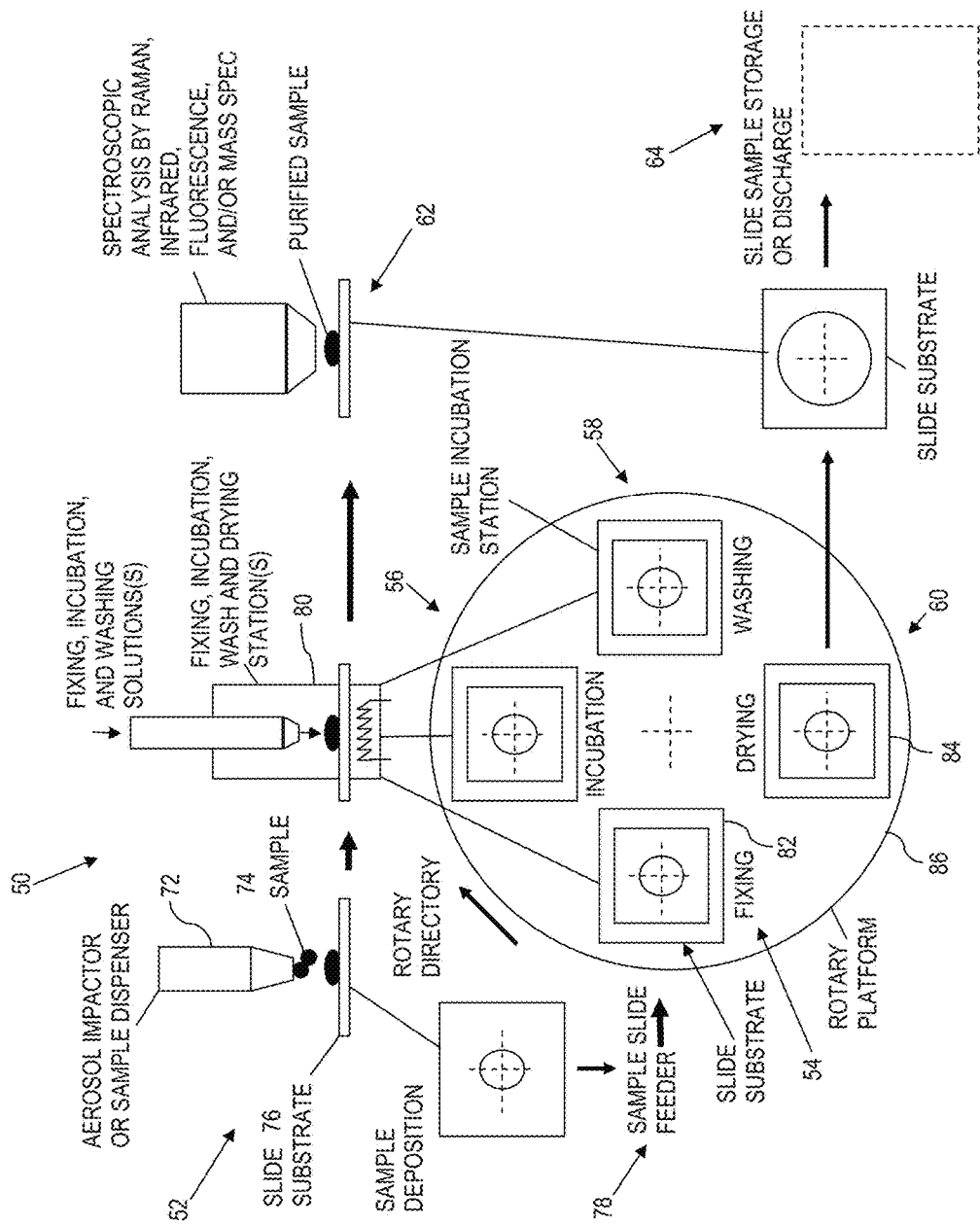
FIG. 2 is an illustration of a system for preparing a sample for spectroscopy analysis according to various aspects of the present disclosure.

FIG. 2 schematically illustrates a single dispenser 80 that is suitably configured to dispense liquids to the slide substrate 76 to implement processes associated with each of the sample fixing station 54, the sample incubation station 56 and the sample washing station 58. However, in practice, the single dispenser 80 can be replaced by dedicated dispensers, e.g., a corresponding dispenser processes associated with each of the sample fixing station 54, the sample incubation station 56 and the sample washing station 58.

After washing, the slide substrate 76 is automatically transitioned to the sample drying station 60 where the collected sample 74 is dried during a drying process. In exemplary implementations, the sample 74 collected on the slide substrate 76 is dried for approximately 20 seconds to approximately 60 seconds with a controlled temperature ranging from approximately 65° C. to approximately 115° C. Also, in exemplary implementations, the sample 74 is dried by feeding the sample substrate 76 onto a heated surface 84, which is heated to a controlled temperature, e.g., in the drying range of from approximately 65° C. to approximately 115° C. In this regard, the heated surface 84 can be similar to the heated surface 82 described with reference to the sample fixing station 52.

The sample 74 on the slide substrate 76, after processing at the drying station 84, has thus retained particles of interest and interferant particles, such as soluble salts and/or non-salt but soluble organic compounds, are removed from the substrate. As such, after the drying process, the sample is cleaned-up and is ready to be presented for analysis, such as by presenting the sample 74 under a spectroscopy of Raman, infrared, fluorescence, spectroscopy, or any combination thereof at the sample analysis station 62. In exemplary implementations, the slide substrate 76 is automatically transitioned from the sample drying station 60 to the sample analysis station 62. In other exemplary implementations, the slide substrate 76 is manually repositioned to the sample analysis station 62. Upon completing the desired analysis, the sample substrate 76 can be transitioned to the sample disposition station 64, e.g., where the sample 74, e.g., where the sample is washed from the sample substrate 76 for recycling. Alternatively, the sample substrate 76 and sample 74 can be preserved, e.g., to maintain a forensics record, the sample substrate 76 can be stored, etc.

In the system 50, which is shown by way of illustration, and not by way of limitation, the slide substrate 76 is automatically transferred from the sample collection station 52 to the sample fixing station 54 by feeding the slide substrate 76 onto a rotational stage 86, e.g., a rotary platform. The rotary platform is utilized to automatically serially feed the slide substrate to the sample fixing station 54, sample incubation station 56, washing station 58 and drying station 60. For example, the slide substrate 76 is then automatically fed from the sample fixing station 54 to the sample incubation station 56, from the sample incubation station 56 to the sample washing station 58, and from the sample washing station 58 to the sample drying station 60 using the rotating stage 86. However, in practice, other and/or alternative stations can be synchronized using a rotating stage, e.g., so that more than four stations are serviced by the rotating stage. As yet another illustrative example, all of the implemented stations can be implemented along a linear stage or other suitable automation system. Still further, in exemplary implementations, transportation of the sample substrate 76 from the rotating stage 86 to the sample analysis station 62 and/or the sample disposition station 64, is implemented using automated stages. In other exemplary implementations, the sample substrate 76 requires some manual intervention, e.g., for placement, alignment, etc., depending upon the particular implementation.

The various stations of the sample processing system 50 can process samples collected onto corresponding slide substrates 76 in a serial, indexed manner, e.g., such that each station simultaneously processes a sample 74 on a corresponding slide substrate 76. In other implementations, there can be deliberate wait states required by various stations to either wait for another station to finish its processing, to spread out processing of sample substrates by the various stations of the sample processing system 50, etc., depending upon the particular implementation.

Moreover, as noted in greater detail above, the process of FIG. 1 and/or the sample processing system 50 of FIG. 2 can remove soluble salts and/or other soluble compounds including organic compounds, potentially completely from a sample. The prefixing solution, incubation solution, and washing solution are pure deionized water or a mixed solution containing alcohols such as ethanol. Other organic solvents can also be added to one or more of the above solutions, depending on the sample nature and sample clean-up requirements. In exemplary implementations, a solvent addition is utilized to minimize dissolution of protein particles of interests and/or to maximize sample cleaning and clean-up effects. That is, the solution(s) can be selected to remove interferant particles from the sample slide while retaining particles of interest on the slide substrate. The organic solvents in the incubation and the washing solutions are removed by a proper heating process at the drying station 60, leaving no (or significantly reduced) background noise to obscure analytical processes and/or results.

As noted above, the sample processing system 50 can clean up contaminants from a sample, retain biological particles (cell, spore, and protein particles) on a slide substrate, and present the cleaned up and/or purified sample for analyses under a spectroscopy that is Raman, infrared, fluorescence, mass spectroscopy, or any combination thereof. In this regard, the various implemented components of the sample processing system 50 can be contained in a unit thus defining a sample processing device. Still further, the sample processing device can be defined by a subset of the illustrated stations. For example, the sample deposition station 52 obtains or otherwise collects samples, and thus defines pre clean-up processing. Correspondingly, the sample analysis station 62 and the sample disposition station 64 perform post clean-up processing. In this regard, a sample clean-up processing device can thus be defined by the stations associated with the rotational stage 86 in the illustrative example, e.g., the sample fixing station 54, the sample incubation station 56, the sample washing station 58 and the sample drying station 60.

The utilization of various stations, 52, 54, 56, 58, 60, 62, 64 permits flexibility in the nature of the collected sample 74. For instance, the sample 74 can comprise an aerosol sample containing microorganism cells, spores, and protein particles, mixed aqueous samples containing microorganism cells and spores, biological monitored samples obtained from ambient air, biological monitored water and environmental samples, medical diagnostic samples for analysis, product samples, etc. However, in practice, the various stations can be combined or otherwise integrated, and/or additional or alternative processing stations can be provided.

Examples of Sample Clean-Up

As noted in greater detail herein, biological samples to be analyzed under a spectroscopy often contain impurities. These biological samples include aerosol samples, biological culture and reagent samples, infectious samples from a patient, water samples, product samples such as in pharmaceuticals, or other mixed samples. The impurities from these samples can create high interfering noise in the analytical process, which can lead ultimately to a failed analysis of these samples.

By way of example, in the spectroscopic detection of microbial cells and spores, inorganic compounds such as ammonium sulfate and other organic compounds are commonly found in ambient aerosol samples or in the biological culture and reagent samples. These inorganic and/or organic compounds are considered impurities. However, the process 10 of FIG. 1 and/or the sample processing system 50 of FIG. 2 are utilized to clean up these impurities and make possible, the detection of vegetative bacterial cells, bacterial spores, and protein aerosol particles with improved accuracy, speed and/or efficiency.

As an illustrative example, mixed aerosol samples containing vegetative microbial cells, spores, and protein particles with ammonium sulfate salt contamination were collected onto slide substrates. The slide substrates including the collected samples were cleaned-up using the process/system set out in greater detail herein with reference to FIGS. 1 and 2. That is, the samples on the slide substrates were processed through a serial operation of fixing, incubation, washing, and drying processes. The cleaned samples were presented to, and analyzed under a Raman spectroscopy. In addition, a vegetative cell sample with a culture medium and salt addition was also tested using the process/system of FIGS. 1 and 2.

Example 1 Ovalbumin Aerosol Clean-Up with Deionized Water

Figure 3:
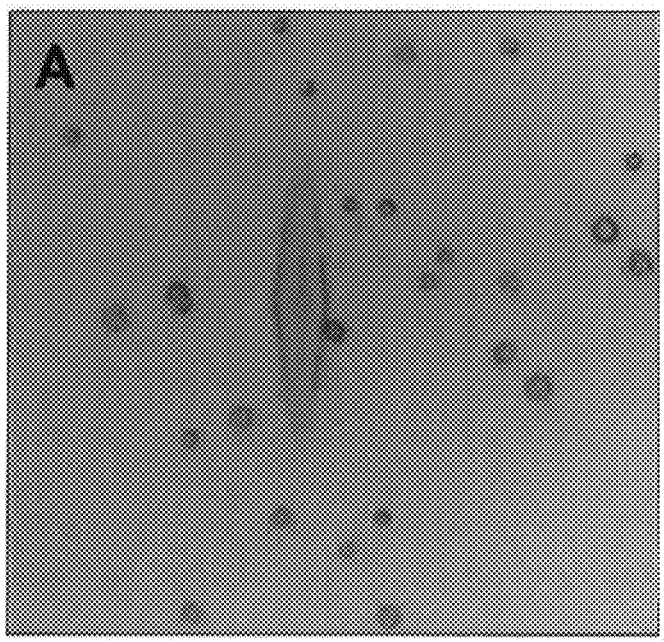
FIG. 3 is a photographic illustration, designated with the reference A, of a sample substrate containing both an Ovalbumin (Ov) aerosol sample and impurities, before cleanup processing using the method of FIG. 1 and/or the system of FIG. 2, according to various aspects of the present disclosure.

Referring to FIG. 3, an Ovalbumin (Ov) protein solution was prepared by mixing an Ov sample in a 0.01 M ammonium sulfate (NH4)2SO4 solution, which was used as a salt contaminant. The Ov solution was then cleaned-up according to the process/system of FIGS. 1 and 2. Particularly, the Ov protein solution was disseminated in a high volume aerosol dissemination system (HV ADS) and was collected onto an aluminum-coated slide substrate with an aerosol impactor. After aerosol collection, the sample fixing process was implemented by fixing the collected sample for 30 seconds at 112° C. After sample fixing, the sample incubation process comprised dispensing deionized water over the sample and holding the sample for 60 seconds. After sample incubation, the sample washing process comprised washing the sample with deionized water. After sample washing, the sample drying process applied a drying heat of substantially 112° C. for 30 seconds. The total process time in this exemplary implementation is 130 seconds or 2.1 minutes.

Figure 4:
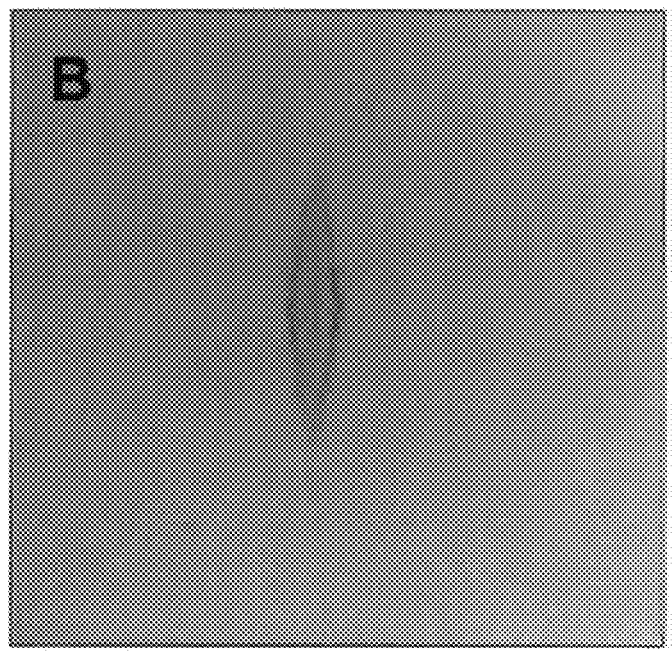
FIG. 4 is a photographic illustration, designated with the reference B, of the Ov aerosol sample of FIG. 3 after implementing sample clean-up using the method of FIG. 1 and/or the system of FIG. 2, using deionized water, according to various aspects of the present disclosure.

The illustration in FIG. 3 shows a 1000× image (designated with the index 'A') of the collected Ov aerosol particles on the slide substrate before clean-up. The Ov solution after clean-up processing is illustrated in the image (designated with the index 'B') of FIG. 4. As illustrated in FIG. 4, the process set out in FIG. 1, using deionized water, washed away the collected Ov aerosol particles from the slide substrate. It is believed that the solubility of Ov particles in deionized water was too high and was dissolved during the incubation and washing process. The diamond shape in each of FIGS. 3 and 4 is an indent marker.

Example 2 Ovalbumin Aerosol Clean-Up with a Mixed Solution

In order to solve the problem encountered in the example described with reference to FIGS. 3 and 4, a 30% ethanol solution was used in the clean-up process described more fully herein. For example, an ethanol solution can dissolve 25% and 13% ammonium sulfate in 15% and 30% ethanol, respectively. Therefore, in exemplary implementations, an ethanol solution is utilized to lower the Ov solubility and maintain salt dissolving capabilities.

Particularly, in a test that included sample clean-up according to the process of FIG. 1, an Ov solution containing contaminants was collected and fixed as set out above with reference to FIGS. 3 and 4. A 30% ethanol solution was then used to incubate the collected Ov aerosol particles. The sample was subsequently washed with deionized water after the incubation and the sample was dried after washing. After the drying process, the Ov sample was presented to a Raman spectroscopy system where the particles on the slide substrate were imaged and analyzed.

Figure 5:
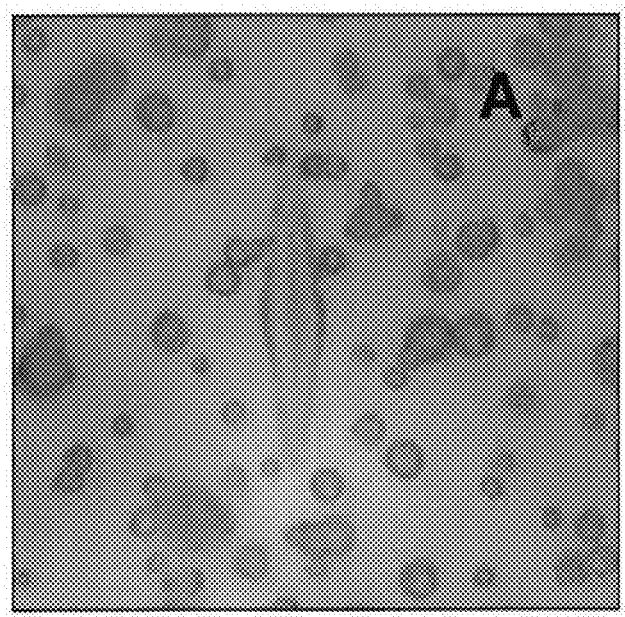
FIG. 5 is a photographic illustration, designated with the reference A, of an Ov aerosol sample with impurities that has been collected on an aluminized slide substrate before cleanup processing using the method of FIG. 1 and/or the system of FIG. 2, according to various aspects of the present disclosure.
Figure 6:
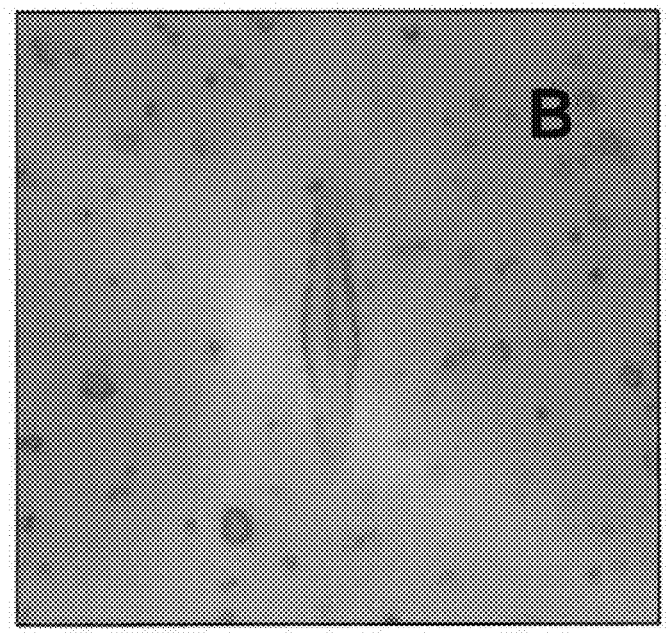
FIG. 6 is a photographic illustration, designated with the reference B, of the Ov aerosol sample of FIG. 5 after implementing sample clean-up using the method of FIG. 1 and/or the system of FIG. 2, using a 30% ethanol solution, according to various aspects of the present disclosure.

The illustration in FIG. 5 shows an image (designated with the index 'A') of the collected Ov aerosol particulates on a slide substrate before processing by the clean-up process set out with regard to FIG. 1. The illustration in FIG. 6 shows an image (designated with the index 'B') of the collected Ov aerosol sample after clean-up according to the process of FIG. 1. In FIGS. 5 and 6, the diamond shape is an indent marker.

Figure 7:
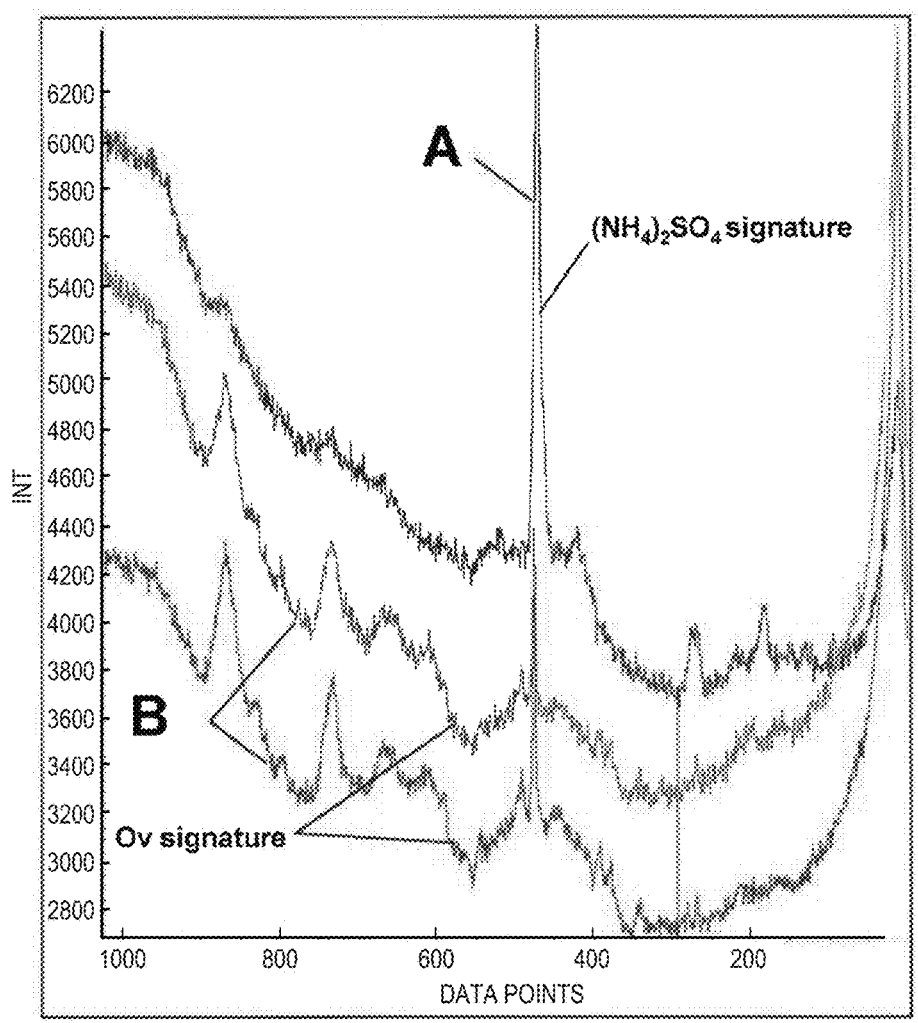
FIG. 7 is a graph that illustrates the resulting spectra of the samples in FIGS. 5 and 6, differentiated by corresponding labels A and B respectively.

Referring to FIG. 7, the Raman spectra of the non-cleaned sample of FIG. 5 (designated with the index 'A') is plotted along with the Raman spectra of the cleaned sample of FIG. 6 (having two traces explained below designated with the index 'B'). As annotated on trace A, corresponding to the spectra of the non-cleaned sample, a large spike between 450 and 500 data points characterizes an ammonium sulfate (NH4)2SO4 signature that dominates the spectrum, indicating noise caused by salt particles. However, the cleaned-up sample (FIG. 6) includes Ov particles that were retained on the slide substrate in such a manner that the Ov spectral signature is revealed in the corresponding Trace B. More particularly, call-out Trace B illustrates two examples of Ovalbumin. The upper trace is grade II Ovalbumin and the lower trace is grade V Ovalbumin. Both traces show that the cleaning is acceptable.

As such, the mixed solution worked effectively in the salt removal process while retaining Ov aerosol particles on the substrate. Particularly, two aerosolized ovalbumin samples, grade II and grade V were demonstrated successfully with the process set out with regard to FIG. 1, using a single 30% ethanol solution in both incubation and washing processes.

Example 3 *Bacillus Cereus* Spore Aerosol Clean-Up with Both Deionized Water and a Mixed Solution As another illustrative example, a *Bacillus cereus* (Bc) spore aerosol sample was cleaned-up using the process/system of FIGS. 1 and 2, using both deionized water and a mixed solution. To test the sample clean-up process, a *Bacilus cereus* spore solution was prepared by mixing a *Bacillus cereus* spore sample in a 0.01 M ammonium sulfate solution, which was used as a salt contaminant to the spore sample. The Bc spore sample was disseminated in a HV ADS and was collected onto an aluminum coated slide substrate with an aerosol impactor.

Figure 8:
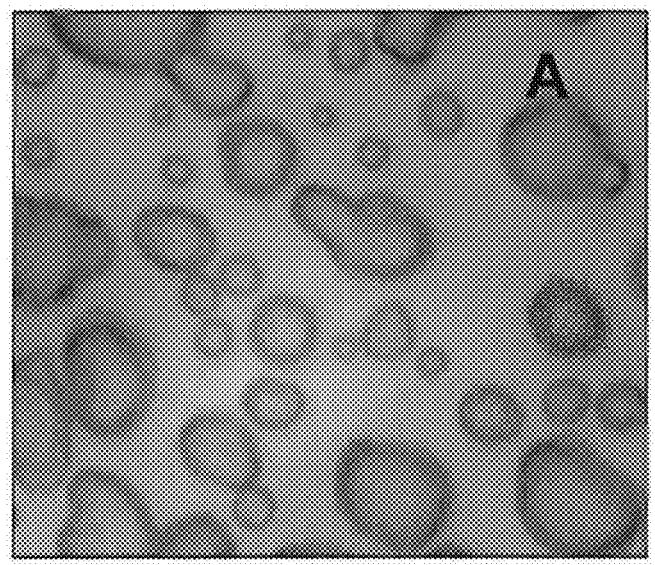
FIG. 8 is a photographic illustration, designated with the reference A, of a *Bacillus cereus* (Bc) aerosol sample with impurities that has been collected on an aluminized slide substrate before cleanup processing using the method of FIG. 1 and/or the system of FIG. 2, according to various aspects of the present disclosure.
Figure 9:
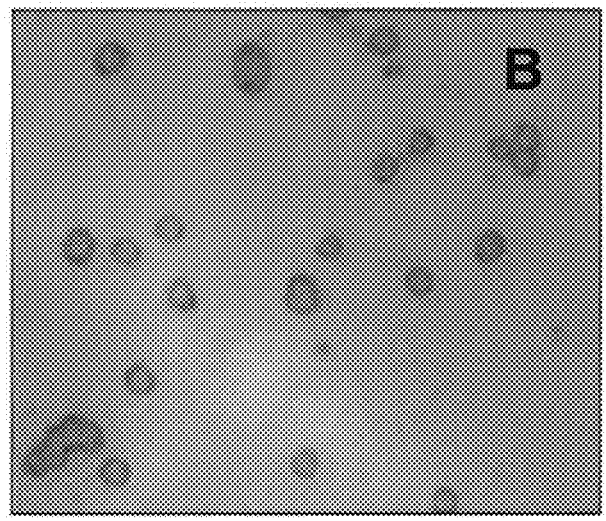
FIG. 9 is a photographic illustration, designated with the reference B, of the Bc aerosol sample of FIG. 8 after implementing sample clean-up using the method of FIG. 1 and/or the system of FIG. 2, according to various aspects of the present disclosure.

FIG. 8 shows a 1000× image (designated with the index 'A') of a Bc spore sample collected onto an aluminized slide substrate before sample clean-up. Particularly, the image shows that the salt contaminant actually covered up the Bc spores. As such, Bc spore morphology was not observed in the sample of FIG. 8. Subsequently, the collected aerosol sample underwent the clean-up process of FIG. 1, utilizing 30 seconds for fixing at 112° C., 60 seconds for incubation with deionized water or a mixed solution containing 30% ethanol, 10 seconds for washing with deionized water, and 30 seconds for drying at 112° C. The total process time was 130 seconds or 2.1 minutes. FIG. 9 shows a 1000× image (designated with the index 'B') of the Bc spore sample after the clean-up process.

Figure 10:
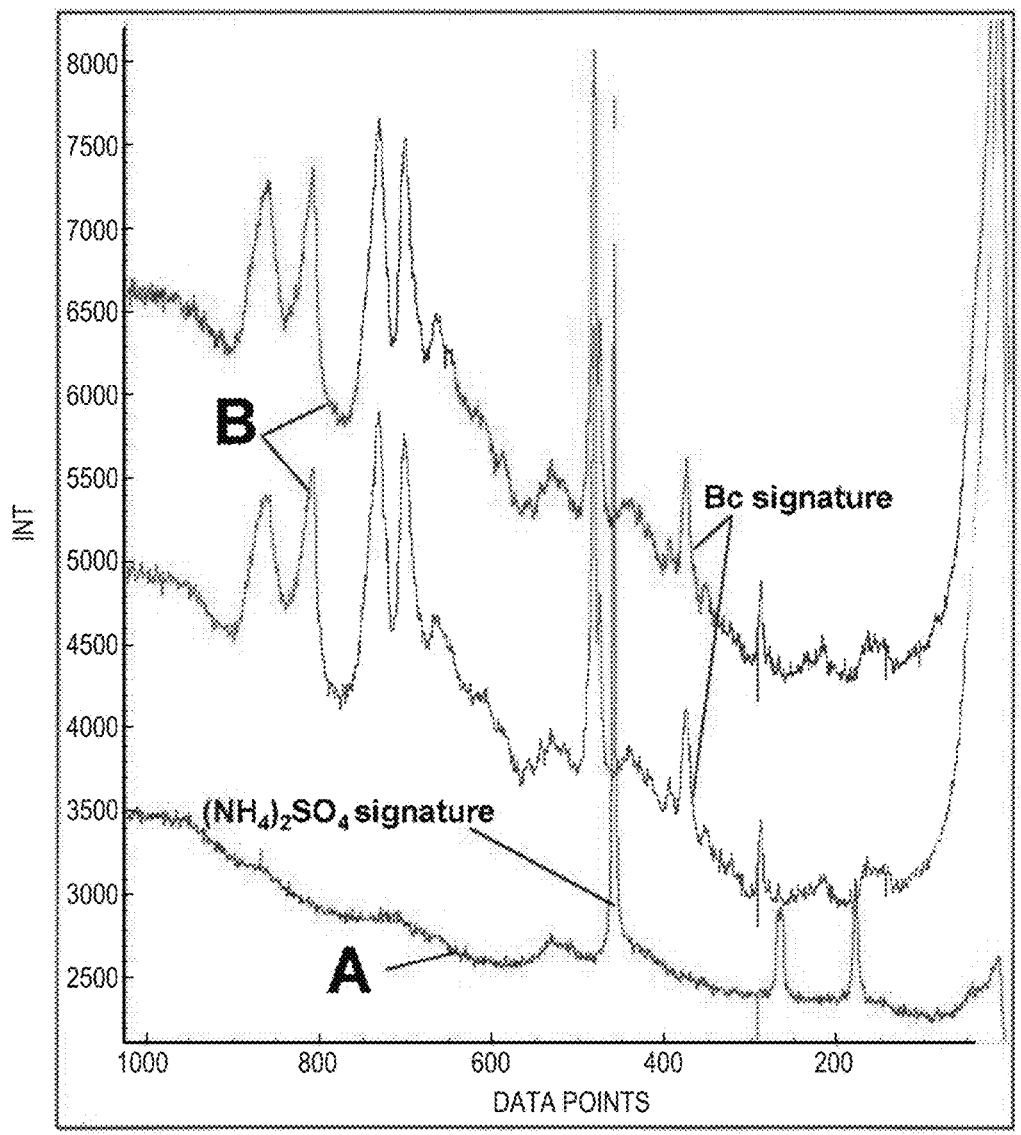
FIG. 10 is a graph that illustrates the resulting spectra of the samples in FIGS. 8 and 9, differentiated by corresponding labels A and B respectively.

Referring to FIG. 10, the Raman spectra of the non-cleaned sample of FIG. 8 (designated with the index 'A') is plotted along with the Raman spectra of the cleaned sample of FIG. 9 (designated with the index 'B'). As annotated on trace A, corresponding to the spectra of the non-cleaned sample, a large spike between 450 and 500 data points characterizes an ammonium sulfate $(NH_4)_2SO_4$ signature that dominates the spectrum, indicating noise caused by salt particles. However, the cleaned-up sample B shows a match with a Bc spore signature. Notably, in various tests, incubations with either deionized water or 30% ethanol solution in the process worked well and could remove ammonium salt effectively from the collected aerosol samples.

Example 4 *Erwinia Herbicola* Aerosol Clean-Up with Both Deionized Water and a Mixed Solution

*Erwinia herbicola* (Eh) is a vegetative bacterial strain. As yet another illustrative example, an *Erwinia herbicola* cell sample was cleaned-up using the process/system of FIGS. 1 and 2, using both deionized water and a mixed solution. To test the sample clean-up process, an *Erwinia herbicola* cell solution was prepared by mixing an *Erwinia herbicola* cell sample in a 0.01 M ammonium sulfate solution, which was used as a salt contaminant to the cell sample. The Eh sample was aerosolized in the HV ADS and the aerosol Eh sample was collected with an impaction collector onto an aluminized slide substrate.

Figure 11:
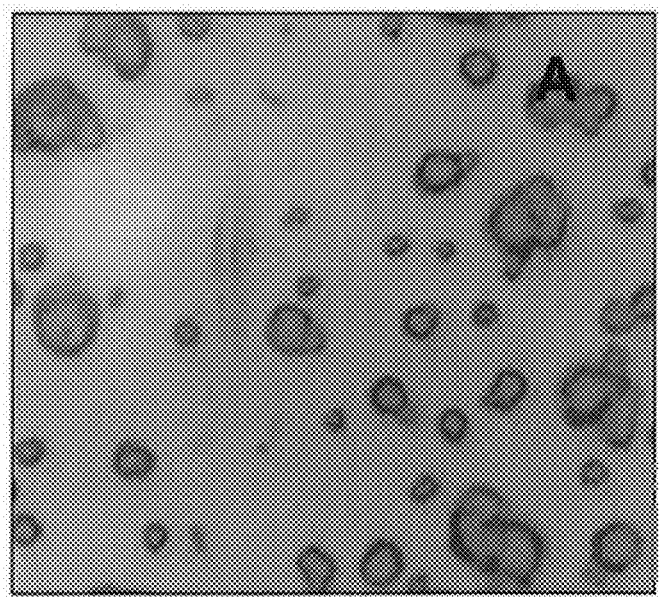
FIG. 11 is a photographic illustration, designated with the reference A, of an *Erwinia herbicola* (Eh) aerosol sample with impurities that has been collected on an aluminized slide substrate before cleanup processing using the method of FIG. 1 and/or the system of FIG. 2, according to various aspects of the present disclosure.
Figure 12:
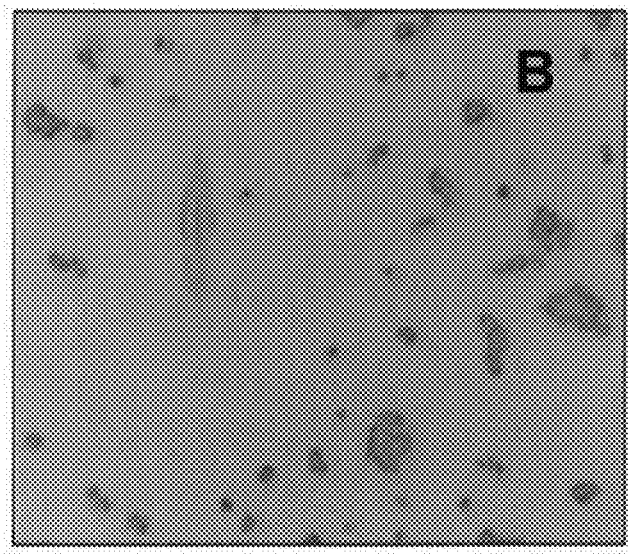
FIG. 12 is a photographic illustration, designated with the reference B, of the Eh aerosol sample of FIG. 11 after implementing sample clean-up using the method of FIG. 1 and/or the system of FIG. 2, according to various aspects of the present disclosure.

FIG. 11 shows a 1000× image (designated with the index 'A') of the Eh sample collected onto an aluminized slide substrate before sample clean-up. Correspondingly, FIG. 12 shows a 1000× image (designated with the index 'B') of the Eh sample after sample clean-up. The diamond shape is an indent marker.

Figure 13:
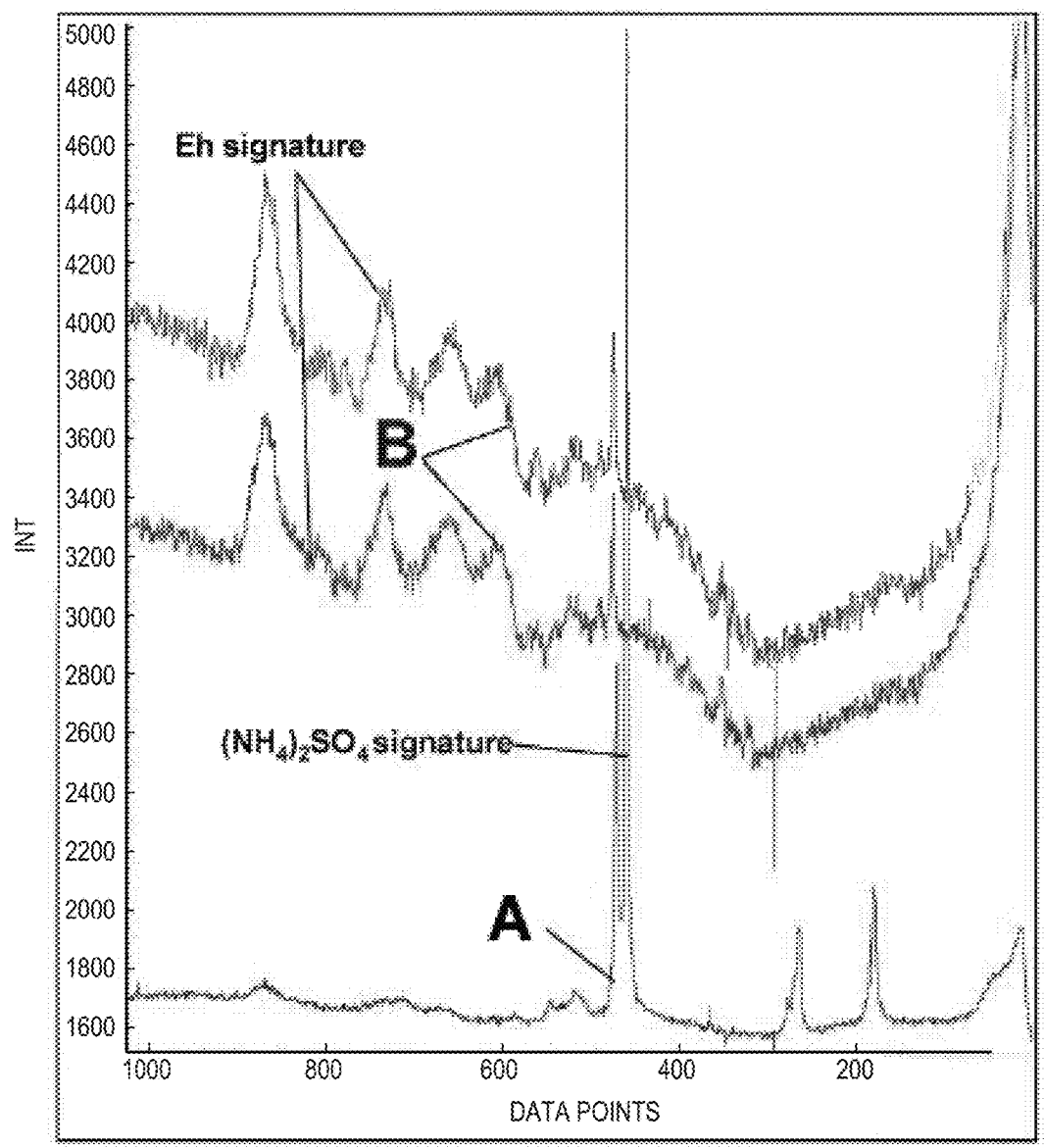
FIG. 13 is a graph that illustrates the resulting spectra of the samples in FIGS. 11 and 12, differentiated by corresponding labels A and B respectively.

Referring to FIG. 13, the Raman spectra of the non-cleaned sample of FIG. 11 (designated with the index 'A') is plotted along with the Raman spectra of the cleaned sample of FIG. 12 (designated with the index 'B'). As annotated on trace A, corresponding to the spectra of the non-cleaned sample, a large spike between 450 and 500 data points characterizes an ammonium sulfate $(NH_4)_2SO_4$ signature that dominates the spectrum, indicating noise caused by salt particles. However, the cleaned-up sample B shows a match with an Eh cell signature. Notably, in various tests, incubations with either deionized water or 30% ethanol solution in the process worked well and could remove ammonium salt effectively from the collected aerosol samples.

Example 5 *Bacilus Globigii* Aerosol Clean-Up with Both Deionized Water and a Mixed Solution

*Bacilus globigii* (Bg) is another spore forming organism. As yet another illustrative example, a Bg spore sample was cleaned-up using the process/system of FIGS. 1 and 2, using both deionized water and a mixed solution. To test the sample clean-up process, a Bg spore solution was prepared by mixing a Bg spore sample in a 0.01 M ammonium sulfate solution, which was used as a salt contaminant to the cell sample. The Bg sample was disseminated in a HV ADS and was collected onto an aluminum coated slide substrate with an aerosol impactor.

Figure 14:
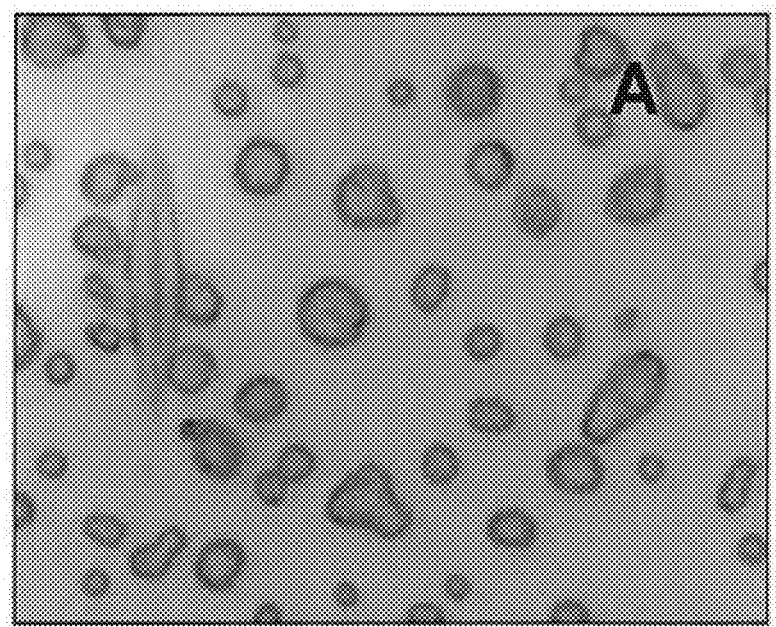
FIG. 14 is a photographic illustration, designated with the reference A, of a *Bacilus globigii* (Bg) aerosol sample with impurities that has been collected on an aluminized slide substrate before cleanup processing using the method of FIG. 1 and/or the system of FIG. 2, according to various aspects of the present disclosure.

FIG. 14 shows a 1000× image (designated with the index 'A') of the Bg sample collected onto an aluminized slide substrate before sample clean-up. As with the Bc sample of Example 3, the image shows that the salt contaminant actually covered up the Bg spores. As such, Bg spore morphology was not observed in the sample of FIG. 14.

Figure 15:
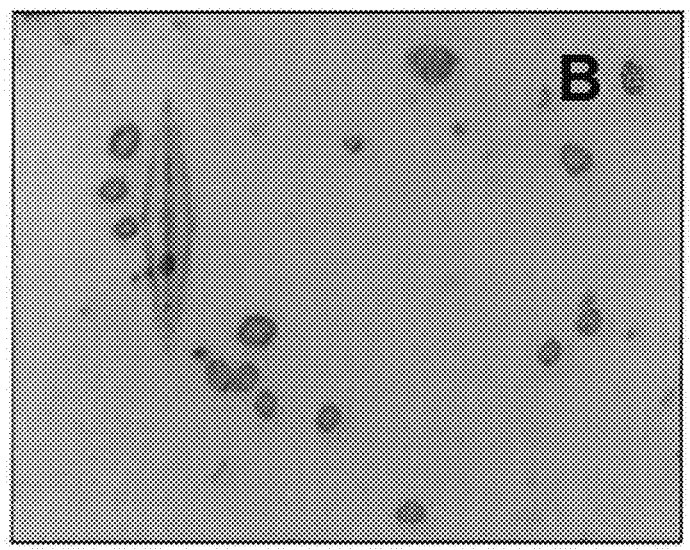
FIG. 15 is a photographic illustration, designated with the reference B, of the Bg aerosol sample of FIG. 14 after implementing sample clean-up using the method of FIG. 1 and/or the system of FIG. 2, according to various aspects of the present disclosure.

Subsequently, the collected sample underwent the clean-up process of FIGS. 1 and 2, utilizing 30 seconds for fixing at 105° C., 20 seconds for incubation with deionized water or a mixed solution containing 30% ethanol, 10 seconds for washing with deionized water or the 30% ethanol solution, and 20 seconds for drying at 105° C. The total process time is 80 seconds or 1.3 minutes. FIG. 15 shows a 1000× image (designated with the index 'B') of the Bg spore sample after the clean-up process. The diamond shape in FIGS. 14 and 15 is an indent marker.

Figure 16:
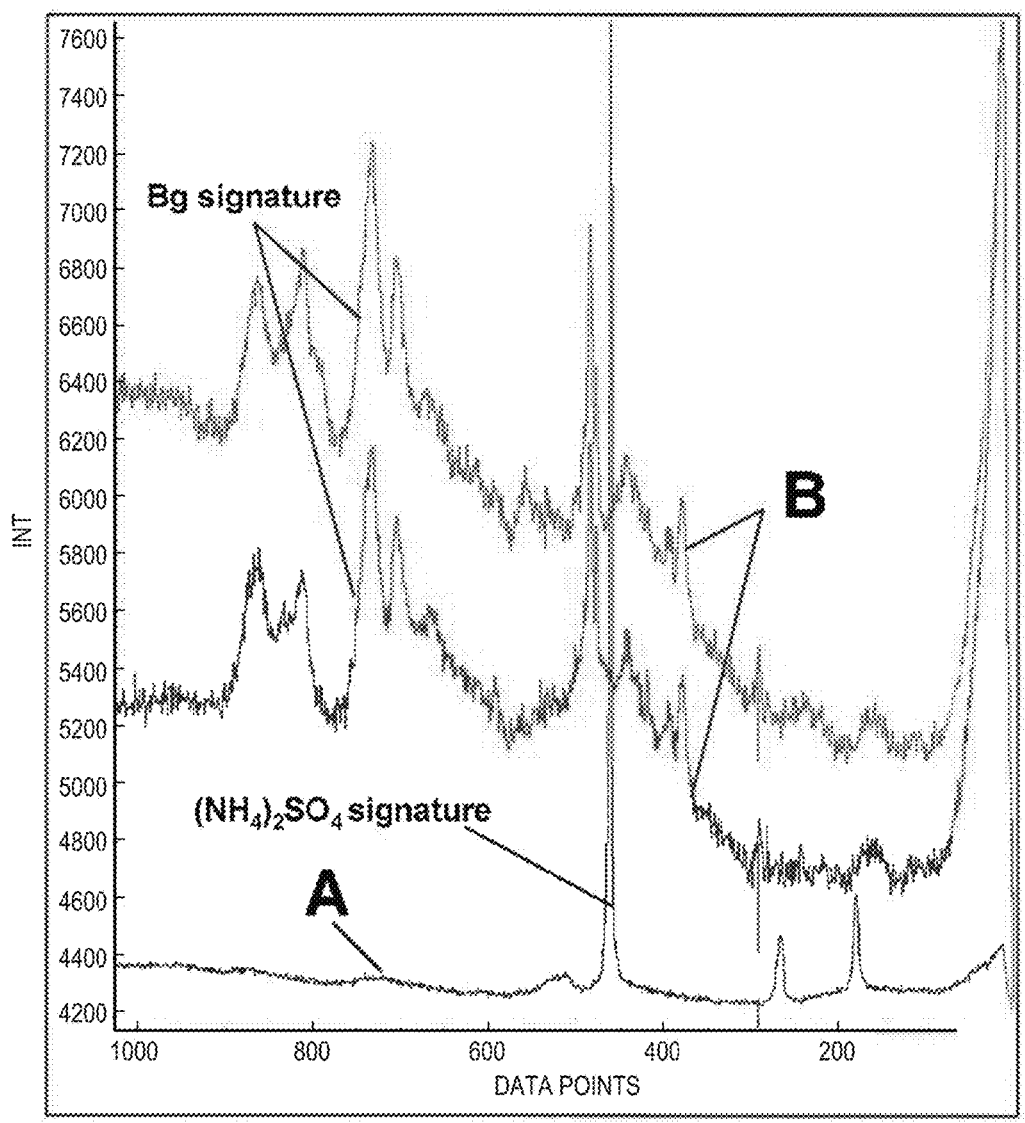
FIG. 16 is a graph that illustrates the resulting spectra of the samples in FIGS. 14 and 15, differentiated by corresponding labels A and B respectively.

Referring to FIG. 16, the Raman spectra of the non-cleaned sample of FIG. 14 (designated with the index 'A') is plotted along with the Raman spectra of the cleaned sample of FIG. 15 (designated with the index 'B'). As annotated on trace A, corresponding to the spectra of the non-cleaned sample, a large spike between 450 and 500 data points characterizes an ammonium sulfate $(NH_4)_2SO_4$ signature that dominates the spectrum, indicating noise caused by salt particles. However, the cleaned-up sample B shows a match with a Bg spore signature. Notably, in various tests, incubations with either deionized water or 30% ethanol solution in the process worked well and could remove ammonium salt effectively from the collected aerosol samples.

Example 6 E *Bacillus Globigii* Spotted Sample Clean-Up with a Mixed Solution

As still another illustrative example, a vegetative *Bacilus globigii* (Bg) cell culture was used as a testing sample for the clean-up process/system of FIGS. 1 and 2. The Bg culture was a mixture of Bg cells and culture medium ingredients containing ammonium sulfate salt. The Bg cell culture was spotted in 5 µl by a micro-pipettor on an aluminized slide substrate. After the spotted sample was dried, the sample was processed under the same conditions as in Example 5.

Figure 17:
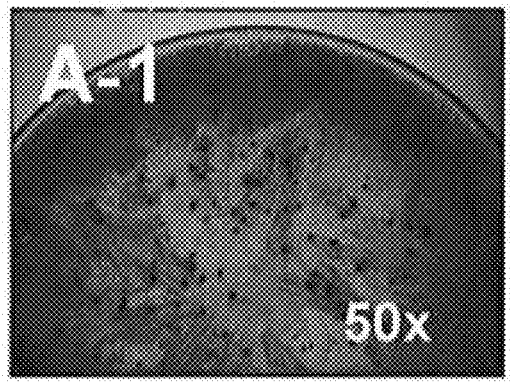
FIG. 17 is a photographic illustration, designated with the reference A-1, of a Bg cell sample at 50× magnification before cleanup processing using the method of FIG. 1 and/or the system of FIG. 2, according to various aspects of the present disclosure.
Figure 18:
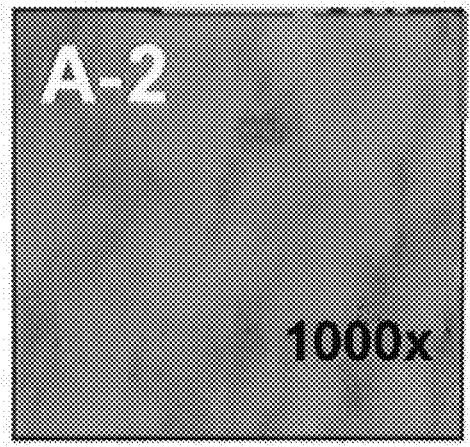
FIG. 18 is a photographic illustration, designated with the reference A-2, of the Bg cell sample of FIG. 17 at 1000× magnification.

FIG. 17 shows an image (designated with the index 'A-1') of the spotted Bg cell sample at 50× magnification before implementing the sample clean-up process of FIG. 1. Correspondingly, FIG. 18 shows an image (designated with the index 'A-2') of the spotted Bg cell sample of FIG. 17 at 1000× magnification. The un-cleaned Bg cell sample was heavily covered with cell culture medium and salt ingredient such that no Bg cells could be observed from the image. Moreover, the un-cleaned Bg sample possessed only the ammonium sulfate salt signature under Raman spectroscopy.

Figure 19:
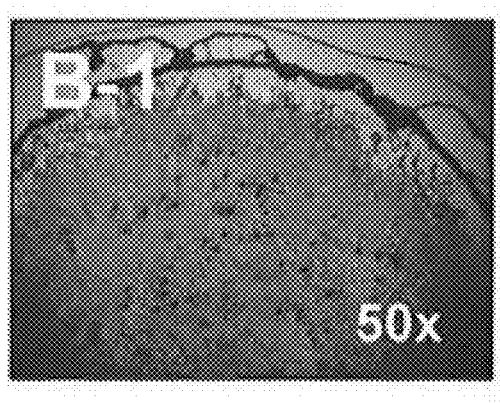
FIG. 19 is a photographic illustration, designated with the reference B-1, of a Bg cell sample at 50× magnification after implementing sample clean-up using the method of FIG. 1 and/or the system of FIG. 2, according to various aspects of the present disclosure.
Figure 20:
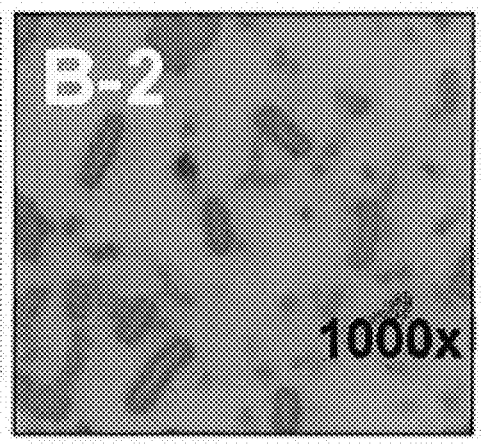
FIG. 20 is a photographic illustration, designated with the reference B-2, of the Bg cell sample of FIG. 19 at 1000× magnification.

FIG. 19 shows an image (designated with the index 13-1') of the spotted Bg cell sample collected onto an aluminized slide substrate at 50× magnification after implementing the sample clean-up process of FIG. 1. Correspondingly, FIG. 20 shows an image (designated with the index 'B-2') of the spotted Bg cell sample of FIG. 19 at 1000× magnification. After the clean-up process, Bg cells could be clearly observed and a Bg cell signature was revealed under Raman spectroscopy.

Figure 21:
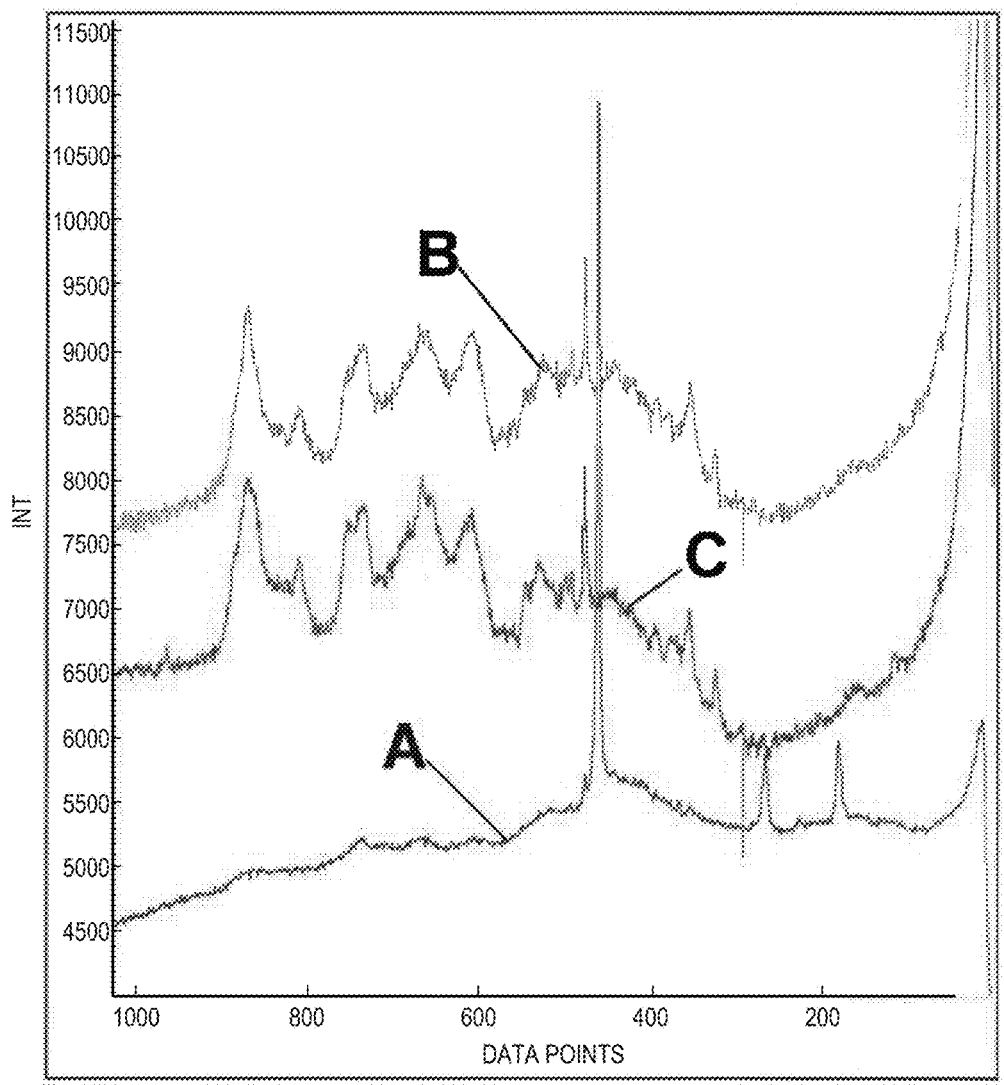
FIG. 21 is a graph that illustrates the resulting spectra of the samples in FIGS. 17-20 respectively, differentiated by corresponding labels A and B respectively.

Referring to FIG. 21, the Raman spectra of the non-cleaned sample of FIGS. 17 and 18 (designated with the index 'A') is plotted along with the Raman spectra of the cleaned sample of FIGS. 19 and 20 (designated with the index 'B'). The trace designated with the index "C" is the spectrum of *Bacilus globigii*. As with the other examples, trace A, corresponding to the spectra of the non-cleaned sample, exhibits a large spike between 450 and 500 data points, which characterizes noise that interferes with the detection of the Bg sample. However, the cleaned-up sample B shows a match with a Bg signature indicated by trace C. The illustrative clean-up process utilized a 30% ethanol solution.

Example 7 *Escherichia Coli* Aerosol Clean-Up with a Mixed Solution

As still another illustrative example, an *Escherichia coli* (*E. coli*) sample was cleaned-up and tested using the process/system of FIGS. 1 and 2. To test the sample clean-up process, an *E. coli* sample was mixed with culture medium ingredients and with 0.01 M ammonium sulfate. The sample suspension was disseminated in a HV ADS and was collected onto an aluminum coated slide substrate with an aerosol impactor.

Figure 22:
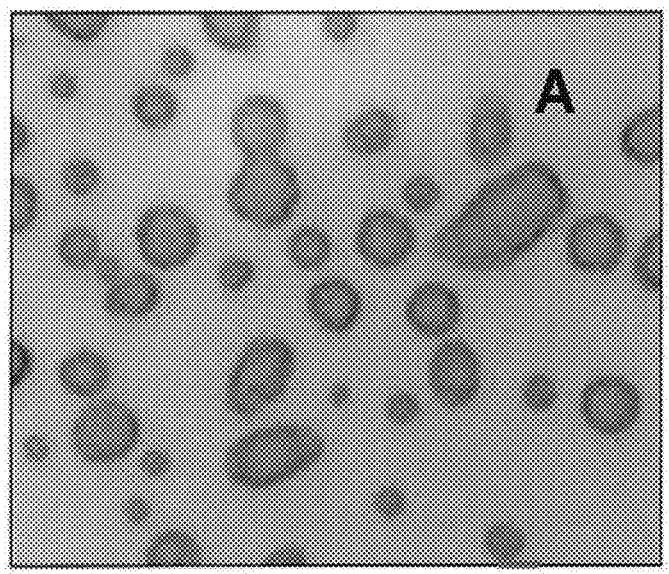
FIG. 22 is a photographic illustration, designated with the reference A, of an *Escherichia coli* (*E. coli*) sample with impurities that has been collected on an aluminized slide substrate before cleanup processing using the method of FIG. 1 and/or the system of FIG. 2, according to various aspects of the present disclosure.

FIG. 22 shows the collected aerosolized *E. coli* sample image (designated with the index 'A'), before sample clean-up. The image shows that the contaminants actually covered up the *E. coli* such that no distinct *E. coli* morphological images were found.

Figure 23:
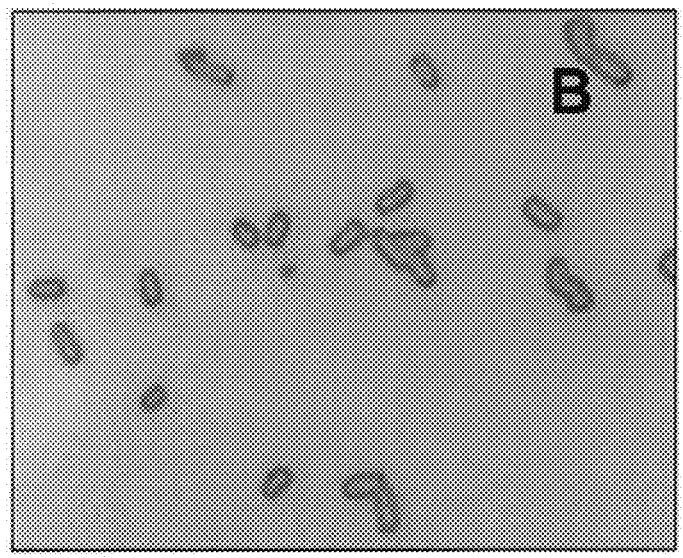
FIG. 23 is a photographic illustration, designated with the reference B, of the *E. coli* sample of FIG. 22 after implementing sample clean-up using the method of FIG. 1 and/or the system of FIG. 2, according to various aspects of the present disclosure.

Subsequently, the collected sample underwent the clean-up process/system of FIGS. 1 and 2, utilizing 30 seconds for fixing at 106° C., 10 seconds for incubation with a mixed solution containing 30% ethanol, 10 seconds for washing with the 30% ethanol solution, and 30 seconds for drying at 106° C. The total process time was 80 seconds or 1.3 minutes. FIG. 23 shows an image (designated with the index 'B') of the *E. coli* sample after the clean-up process. After the clean-up process, *E coli* cells could be easily seen from the image.

Figure 24:
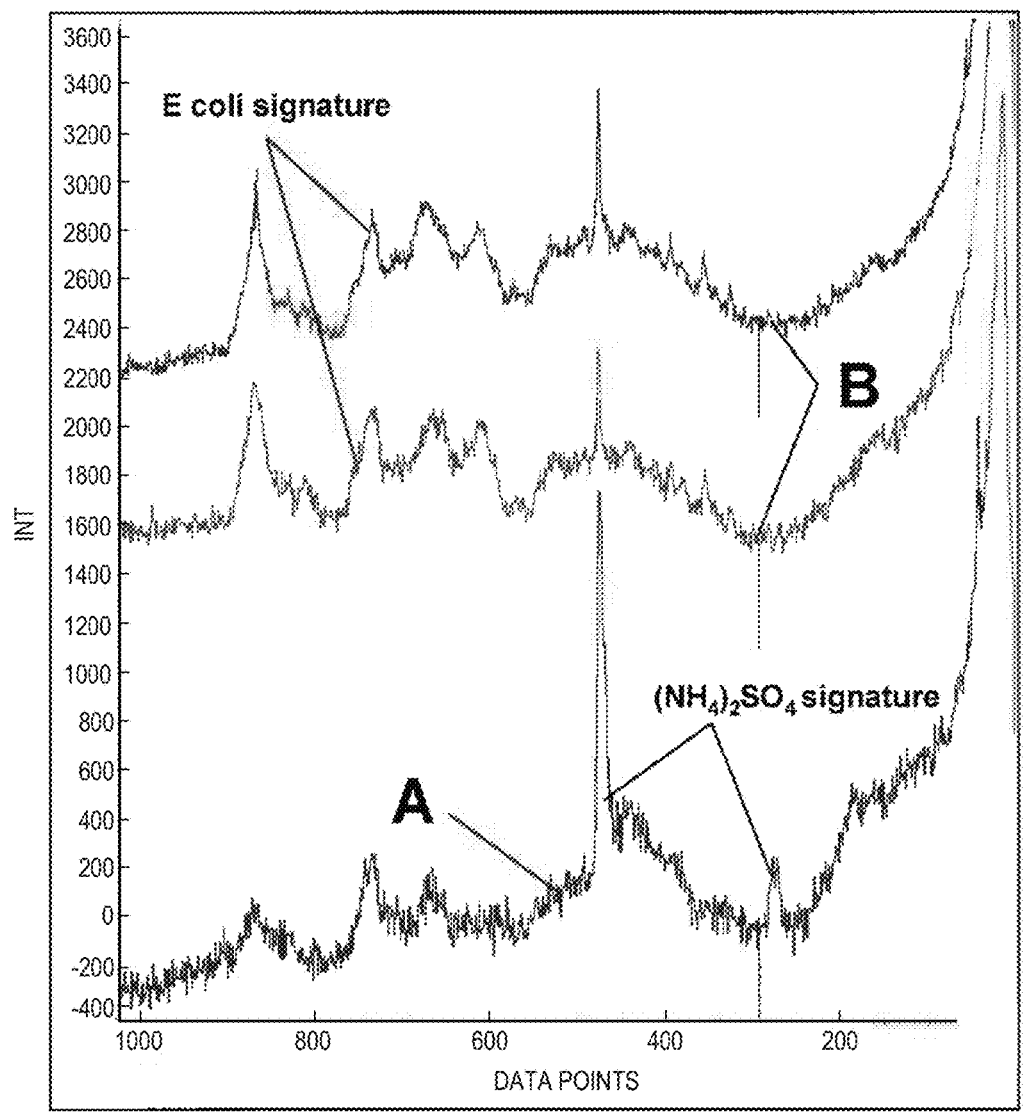
FIG. 24 is a graph that illustrates the resulting spectra of the samples in FIGS. 22 and 23, differentiated by corresponding labels A and B respectively.

Referring to FIG. 24, the Raman spectra of the non-cleaned sample of FIG. 22 (designated with the index 'A') is plotted along with the Raman spectra of the cleaned sample of FIG. 23 (designated with the index 'B'). As annotated on trace A, corresponding to the spectra of the non-cleaned sample, a large spike between 450 and 500 data points characterizes an ammonium sulfate (NH4)2SO4 signature that dominates the spectrum, indicating noise caused by contaminants. However, the cleaned-up sample B shows a match with an *E. coli* signature. Incubation with a 30% ethanol solution worked well and could remove ammonium salt completely from the collected aerosol samples.

Example 8 *Bacillus Thuringiensis* Aerosol Clean-Up with a Mixed Solution

Dipel is a commercially available insecticide that contains a fractional active ingredient, *Bacilus thuringiensis* (Bt). In yet another illustrative test, a sample was prepared by adding 0.01 M ammonium sulfate to a Dipel suspension, which was then disseminated in the HV ADS and was collected onto an aluminum coated slide substrate with an aerosol impactor.

Figure 25:
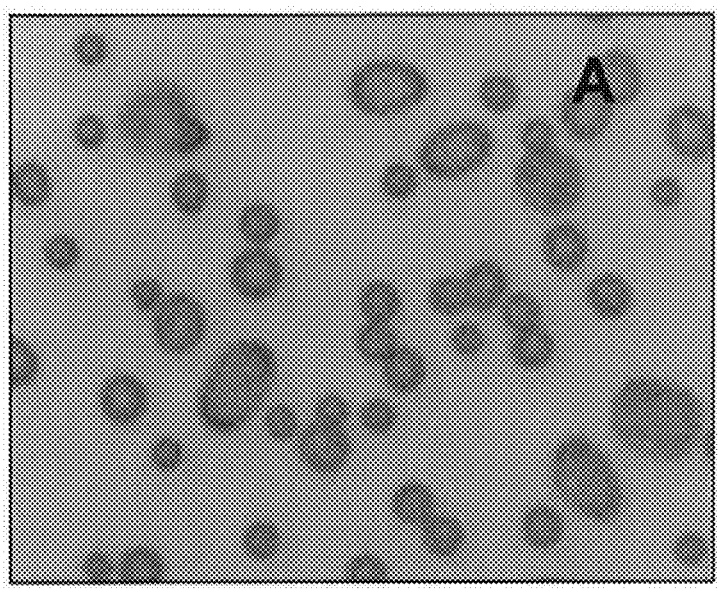
FIG. 25 is a photographic illustration, designated with the reference A, of a *Bacilus thuringiensis* sample with impurities that has been collected on an aluminized slide substrate before cleanup processing using the method of FIG. 1 and/or the system of FIG. 2, according to various aspects of the present disclosure.
Figure 26:
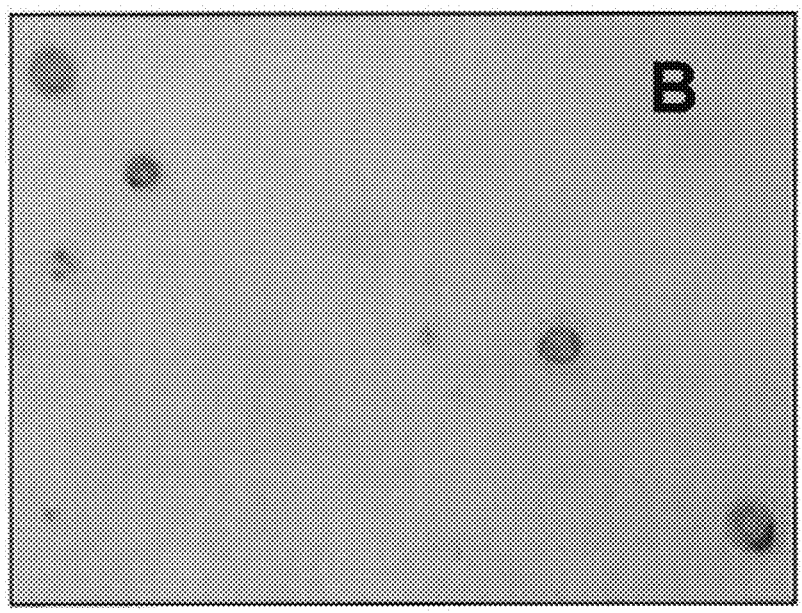
FIG. 26 is a photographic illustration, designated with the reference B, of the *Bacilus thuringiensis* sample of FIG. 25 after implementing sample clean-up using the method of FIG. 1 and/or the system of FIG. 2, according to various aspects of the present disclosure.

FIG. 25 shows the collected Bt sample image (designated with the index 'A'), before sample clean-up. Subsequently, the collected sample underwent the clean-up process/system of FIGS. 1 and 2, utilizing 30 seconds for fixing at 106° C., 10 seconds for incubation with a mixed solution containing 30% ethanol, 10 seconds for washing with the 30% ethanol solution, and 30 seconds for drying at 106° C. The total process time is 80 seconds or 1.3 minutes. FIG. 26 shows the collected Bt sample image (designated with the index 'B'), after the clean-up process. After the clean-up process, Bt spores could be easily seen from the image.

Figure 27:
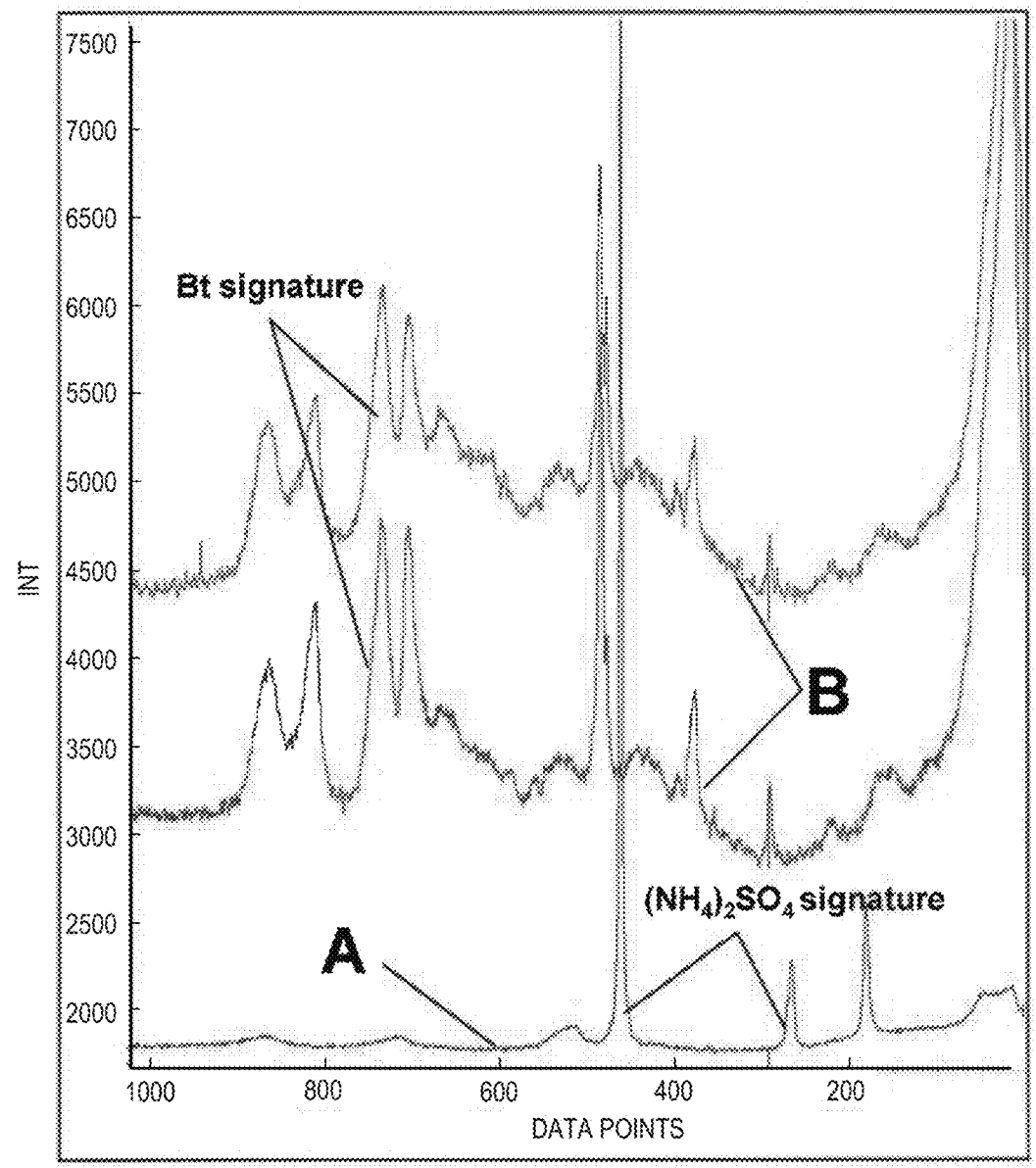
FIG. 27 is a graph that illustrates the resulting spectra of the samples in FIGS. 25 and 26, differentiated by corresponding labels A and B respectively.

Referring to FIG. 27, the Raman spectra of the non-cleaned sample of FIG. 25 (designated with the index 'A') is plotted along with the Raman spectra of the cleaned sample of FIG. 26 (designated with the index 'B'). As annotated on trace A, corresponding to the spectra of the non-cleaned sample, a large spike between 450 and 500 data points characterizes an ammonium sulfate (NH4)2SO4 signature that dominates the spectrum, indicating noise caused by contaminants. However, the cleaned-up sample B shows a match with a Bt signature. Incubation with a 30% ethanol solution worked well and could remove ammonium salt completely from the collected aerosol samples.

General Observations

The processes and systems set out more fully herein can handle microgram ($\mu$g) or even nanogram (ng) aerosol materials. Under a control condition, one impaction-collected aerosol sample on an aluminized substrate is approximately 1.5 mm in diameter. If one field of view (FOV) is defined as 0.10 mm×0.10 mm, one collected sample would have about 176 FOVs. If each FOV is covered by a monolayer of approximately 4000 one micron particles, the total weight of the particles would be about 0.7 $\mu$g (700 ng), assuming that one particle weighs $1 \times 10^{-12}$ g.

The processes and systems set out more fully herein only require a minimum processing solution, e.g. 30% ethanol. For each assay, only 5 $\mu$l mixed solution is required in the incubation process and 0.8 ml mixed solution is used in the washing process. In this regard, fix and wash operations have minimum fluid handling and can be automated, e.g., as set out with regard to FIG. 2. Still further, as described with reference to FIG. 2, the fix and wash processes described herein can be integrated with sample collection and/or fluidic dispensing systems as also illustrated with reference to FIG. 2. Further optimization can reduce this amount, possible down to 0.5 ml. Accordingly, the clean-up process, e.g., as described with reference to FIG. 1, has minimum fluid handling and can be easily automated, e.g., in the system 50 of FIG. 2. Moreover, the clean-up process can be easily integrated with a sample collector or fluidic sample dispensing system as described with reference to FIG. 2.

Still further, the sample processing time can occur in approximately 1.3-2.1 minutes. The process time can be further optimized and could be shorter, depending upon sample collection and other factors.

Biological Sequestration on a Culturable and Raman Silent Substrate

According to still further aspects of the present disclosure, systems and methods are provided for increasing the collection efficiency of impacted biological aerosols in addition to providing a substrate that can be used to support the post-process culturability of a sampled organism. The support of post-process culturability of a sampled organism can enable the growth of viable materials without having to remove the organisms from the impaction substrate and risk losing material, e.g., in the transfer to an Agar plate.

Figure 28:
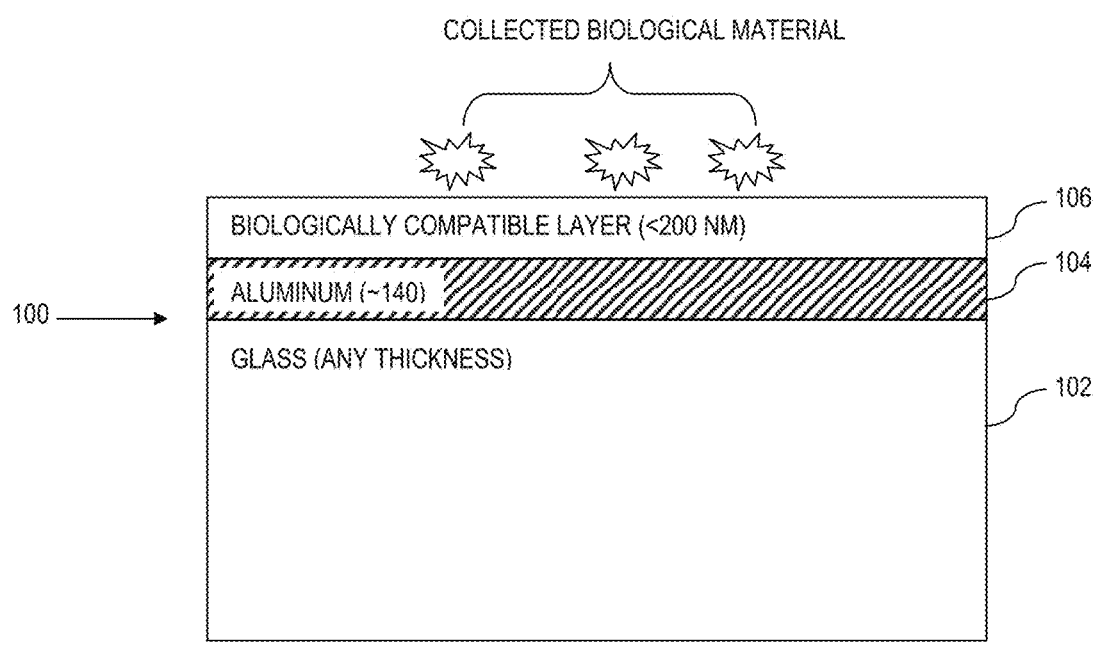
FIG. 28 is a schematic illustration of a slide substrate according to various aspects of the present disclosure.

Referring to FIG. 28, according to still further aspects of the present disclosure, a substrate 100 is provided that includes a Raman silent biological capture material. Thus, the substrate does not contribute to the measured spectra of the organism that it supports.

In an example implementation, the Raman silent substrate comprises a base, and a biologically compatible material layer over the base, where the biologically compatible material layer is Raman silent, provides a predetermined capture efficiency corresponding to a desired application, and supports biological culturing. More particularly, the biologically compatible material layer is Raman silent to the extent that the Raman silent substrate does not contribute to a Raman signature collected during a spectroscopic evaluation of a biological target collected upon the Raman silent substrate. Also, the biologically compatible material layer provides a predetermined capture efficiency of the Raman signature collected during the spectroscopic evaluation, and supports biological culturing of the biological target collected upon the substrate.

For instance, in the example implemented with regard to FIG. 28, the base of the Raman silent substrate 100 is composed of a glass layer 102, as well as an aluminum layer 104 over the glass layer 102. A biologically compatible material layer 106 is over the base. As such, the aluminum layer 104 is situated between the glass layer 102 and the biologically compatible material layer 106. The example Raman silent substrate 100 is thus configured such that the biologically compatible material layer 106 is Raman silent, provides a predetermined capture efficiency corresponding to a desired application, and supports biological culturing, as described more fully herein.

In an illustrative example, the glass layer 102 comprises a borosilicate or similar glass material. Moreover, the thickness of the glass layer 102 can be selected based upon the particular application or other determining factors.

In a further illustrative example implementation, the aluminum layer 104 can comprise up to a one-hundred-and-forty nanometer (nm) thick planar aluminum coating. The aluminum layer 104 can be deposited onto one surface of the supporting glass layer 102, for instance, via ion assisted deposition, evaporation, or similar method.

According to further aspects of the present disclosure, the flatness and roughness of the Raman silent substrate 100 preferably mimics the flatness and roughness of the glass layer 102. Preferably, the flatness and roughness of the glass layer 102 should not exceed $\lambda/10$ and 60-40 scratch-dig. In this regard, $\lambda$ corresponds to the wavelength of the laser source used in a corresponding spectroscopic analysis system for which the Raman silent substrate 100 is utilized.

In addition to the above, the Raman silent substrate 100 can include one or more biologically compatible material layers (collectively 106) that are over the base, e.g., the aluminum layer 104 in the illustrative example, to provide desired functionality. For example, several materials have been identified and successfully deposited on the aluminum layer 104 that perform at least one function, such as to increase the capture efficiency or otherwise provide suitable capture efficiency for a desired application, provide a Raman silent layer, and/or support biological culturing.

As a few non-limiting but illustrative examples, the biologically compatible material layer (or layers) 106 can include any one or more of the following characteristics, either alone or in combination with other described characteristics.

The biologically compatible material layer 106 can comprise a thicknesses less than a wavelength of light divided by two times a numerical aperture ($\lambda/(2^*NA)$) of collection optics of a corresponding spectroscopic system.

Yet further, the biologically compatible material layer 106 can comprise a biologically compatible material with a small Raman cross-section. Notably, the power of scattered light in a Raman spectroscopic system is typically equal to the product of the intensity of the incident photons and a term known as the Raman cross-section. The Raman cross-section is proportional to a function of the wavelength of the incident photons produced by a corresponding Raman spectroscopic system. As such, in this example implementation, the biologically compatible material layer comprises a biologically compatible material having a Raman cross-section smaller than a predetermined Raman cross-section selected according to the spectroscopic evaluation.

Still further, the biologically compatible material layer 106 can comprise a biologically compatible material that is free of (or have a minimal content of) symmetrical molecular moieties (such as tryptophan) and/or is further free of unsaturated chemical bonds.

According to still further aspects, the biologically compatible material layer 106 can comprise a biologically compatible material having a low opacity at an excitation laser wavelength of a laser source in a corresponding spectroscopic system. In spectroscopic systems that incorporate fluorescence, the biologically compatible material layer 106 can further be selected from a material that has no fluorescence response.

Still further, the biologically compatible material layer 106 can comprise a non-selective binding material that promotes adhesion. For instance, example non-selective binding material can comprise at least one of collagen, poly-lysine, poly-ornithine, fibronectin, laminin, other chemicals, combinations thereof, etc. This can reduce the mobility of the biological material during analysis. Similarly, the biologically compatible material layer 106 can comprise a selective binding material including (or such as) an antibody. This also can reduce the mobility of targeted biological material during analysis.

In yet further embodiments, the biologically compatible material layer 106 can comprise a biofilm, e.g., which is associated with a biological material under examination. Likewise, the biologically compatible material layer 106 can comprise a hydrophilic material or a hydrophobic material corresponding to a hydrophobicity of a biological material of interest. Still further, the biologically compatible material layer 106 can comprise a biological compatible material that does not selectively bind calcium ions, sodium ions, and/or potassium ions and does not significantly suppress ion diffusion in condensed phase solutions. For instance, the biologically compatible material layer 106 can comprise a biologically compatible thin film having a thickness of 1 to 150 nanometers.

In still further embodiments, the base can comprise a metalized portion (e.g., as noted above, the base can comprise a glass layer 102 and an aluminized layer 104). In this configuration, the biologically compatible material layer 106 can include a material configured to prevent an exchange of metal ions between the metallized portion and biological material collected upon the substrate.

As a particular working example, the biologically compatible material layer 106 can include Poly-l-lysine and Agarose. Moreover, Agarose can be modified to provide differing degrees of resilience (i.e., spongy or rubbery) to suit a particular application. The resilience can be modified, for example, by changing the amount of water in the Agarose.

Figure 29:
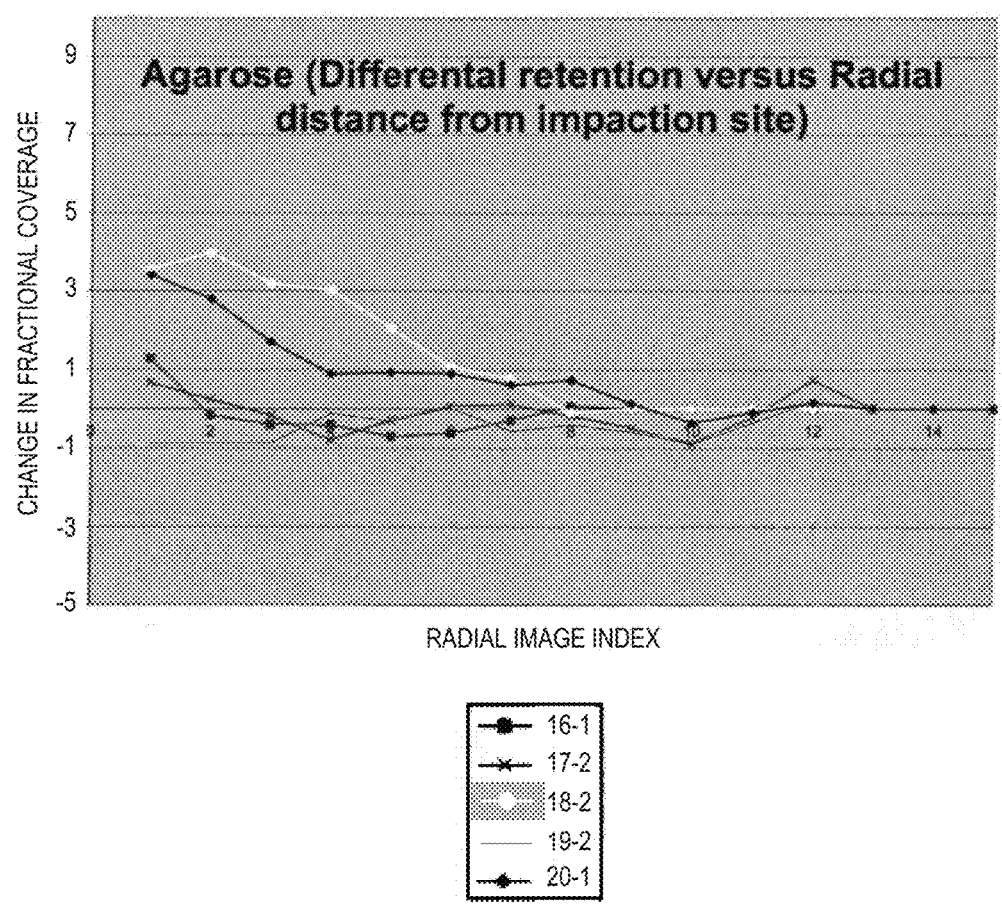
FIG. 29 is a chart illustrating differential retention versus the radial distance from the impaction site for a test involving Agarose.

Poly-l-lysine can be controllably deposited in a variety of different thicknesses from a monolayer to a film several hundreds of nanometers thick. Both Poly-l-lysine and Agarose show a degree of capture efficiency improvement. The enhanced performance of the Raman silent substrate 100 can be due to a more resilient surface capable of dissipating the kinetic energy of the impacted particles, which reduces particles lost due to rebounding off the surface. The enhanced performance of the Raman silent substrate 100 can also be due to the provision of a surface that can hydrogen bond or have a specific interaction with the surface of the biological entity being collected, which prevents particles lost after initial capture. For instance, referring to FIG. 29, a chart plots the differential retention versus the radial distance from the impaction site for a test involving Agarose.

Certain biologically compatible materials useful in slide substrates are not Raman silent and thus can thus have a significant Raman signature. However, according aspects of the present disclosure, a biologically compatible material that has a Raman signature can be utilized to form the biologically compatible material layer 106 by controlling the thickness of the biologically compatible material layer 106 to approximately 200 nm or less. In this regard, the biologically compatible material layer 106 can be controlled to limit the layer buildup, e.g., on the aluminum layer 104, or the biologically compatible material layer 106 on the aluminum layer 104 can otherwise be reduced to a thickness of 200 nm or less.

Particularly, it was found that if the thickness of the biologically compatible material layer 106 is reduced to approximately 200 nm or less, it does not contribute to the Raman signature of the collected biological target. The "Raman silence" is believed to be achieved because the volume of material within the optical interrogation volume is less than the detection limit of the Raman spectroscopic instrument. This premise can be expanded to include optical methods that further reduce the Raman interrogation volume. Such techniques include confocal or diffraction limited Raman excitation followed by an optically complementary spatial filter before the Raman spectrometer/detector.

Using the above-described optical techniques, a larger selection of materials can be selected from to define the biologically compatible material layer 106, where the selected material could, for example, serve the same purpose as the above-described Agarose and/or Poly-l-lysine. Moreover, such alternative materials can have greater ability to retain/sequester biological materials and/or such materials can be easier to process.

Tests indicated that materials such as Agarose and/or Poly-l-lysine can be utilized to define the biologically compatible material layer 106 so as to not show significant fluorescence when excited with 250-405 nm radiation. Additionally, Raman field-of-view imaging can be accomplished without a significant CH stretch background. This will enable fluorescence based and CH Raman based biological targeting.

These materials can also be used to culture biological organisms. As such, the biologically compatible material layer 106 can be utilized to both retain biological material more efficiently from the collector/impactor and also support biological culturing directly on the supported substrate after presumptive identification. The latter step eliminates the need to elute the biological material of interest onto a second substrate for culturing.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention.

Having thus described the invention of the present application in detail and by reference to embodiments thereof, it will be apparent that modifications and variations are possible without departing from the scope of the invention defined in the appended claims.

What is claimed is:

1. A Raman silent substrate comprising:
 a base having:
  a glass layer; and
  a planar aluminum layer over the glass layer, where the aluminum layer is up to 140 nanometers thick; and
 a Raman silent capture means for capturing a biological target on the Raman silent substrate such that the Raman silent capture means does not contribute to a Raman signature collected during a spectroscopic evaluation of the biological target when collected upon the Raman silent substrate;
 wherein:
  the Raman silent capture means is over the aluminum layer of the base; and
  a flatness of the Raman silent substrate mimics a flatness of the base.

2. The Raman silent substrate according to claim 1, wherein:
 the Raman silent capture means captures a biological target on the Raman silent substrate such that the Raman silent capture means does not contribute to a Raman signature collected during a spectroscopic evaluation by implementing a biologically compatible thin film having a thickness of 1 to 150 nanometers.

3. The Raman silent substrate according to claim 1, wherein:
 the Raman silent capture means captures a biological target on the Raman silent substrate such that the Raman silent capture means does not contribute to a Raman signature collected during a spectroscopic evaluation by implementing a thicknesses less than a wavelength of light divided by two times a numerical aperture of collection optics of a corresponding spectroscopic system.

4. The Raman silent substrate according to claim 1, wherein:
 the Raman silent capture means captures a biological target on the Raman silent substrate such that the Raman silent capture means does not contribute to a Raman signature collected during a spectroscopic evaluation by implementing a biologically compatible material having a Raman cross-section smaller than a predetermined Raman cross-section selected according to the spectroscopic evaluation, where the Raman cross-section is proportional to a function of a wavelength of incident photons produced by a corresponding Raman spectroscopic system.

5. The Raman silent substrate according to claim 1, wherein:
the Raman silent capture means captures a biological target on the Raman silent substrate such that the Raman silent capture means does not contribute to a Raman signature collected during a spectroscopic evaluation by implementing a biologically compatible material that is free of symmetrical molecular moieties and is further free of unsaturated chemical bonds.

6. The Raman silent substrate according to claim 1, wherein:
the Raman silent capture means captures a biological target on the Raman silent substrate such that the Raman silent capture means does not contribute to a Raman signature collected during a spectroscopic evaluation by implementing a biologically compatible material that includes agarose and/or poly-l-lysine arranged such that Raman field of view imaging is accomplished without CH stretch background and an excitation laser wavelength of a laser source in a corresponding spectroscopic system between 250-405 nanometers does not cause the Raman silent capture means to fluoresce.

7. The Raman silent substrate according to claim 1, wherein:
the Raman silent capture means further comprises at least one of a non-selective binding material that promotes adhesion, and a material that supports biological culturing of the biological target collected upon the substrate.

8. The Raman silent substrate according to claim 7, wherein:
the non-selective binding material comprises at least one of collagen, poly-lysine, poly-ornithine, fibronectin, and laminin.

9. The Raman silent substrate according to claim 1, wherein:
the Raman silent capture means comprises a selective binding material including an antibody.

10. The Raman silent substrate according to claim 1, wherein:
the Raman silent capture means comprises a biofilm that is associated with a biological material under examination.

11. The Raman silent substrate according to claim 1, wherein:
the Raman silent capture means comprises a select one of a hydrophilic-material, and a hydrophobic material corresponding to a hydrophobicity of a biological material of interest.

12. The Raman silent substrate according to claim 1, wherein:
the base comprises a metalized portion; and
the biologically compatible material layer is a material configured to prevent an exchange of metal ions between the metallized portion and biological material collected upon the substrate.

13. The Raman silent substrate according to claim 1, wherein:
the Raman silent capture means comprises a biological compatible material that does not selectively bind calcium ions, sodium ions, and potassium ions.

14. The Raman silent substrate according to claim 1, wherein:
the Raman silent capture means does not significantly suppress ion diffusion in condensed phase solutions.

15. The Raman silent substrate according to claim 1, wherein:
the flatness of the glass layer does not exceed $\lambda/10$ and a roughness of the glass layer does not exceed 60-40 scratch-dig, wherein $\lambda$ corresponds to a wavelength of a laser source used in a corresponding spectroscopic analysis system for which the Raman silent substrate is utilized.

16. The Raman silent substrate according to claim 1, wherein:
the Raman silent capture means is less than 200 nanometers thick.

17. A method of preparing a Raman silent substrate, comprising:
providing a base by:
providing a glass layer; and
depositing an aluminum layer up to 150 nanometers thick as a planar aluminum coating;
wherein a flatness and roughness of the glass layer does not exceed $\lambda/10$ and 60-40 scratch-dig, where $\lambda$ corresponds to a wavelength of a laser source used in a corresponding spectroscopic analysis system for which the Raman silent substrate is utilized;
providing a biologically compatible material layer over the base, such that a flatness of the Raman silent substrate mimics a flatness of the base, wherein the biologically compatibly layer is selected for producing a Raman silent response to the extent that the Raman silent substrate does not contribute to a Raman signature collected during a spectroscopic evaluation of a biological target collected upon the Raman silent substrate.

18. The method of claim 17, wherein the biologically compatible layer includes at least one of Poly-l-lysine and Agarose, further comprising:
controllably depositing the Poly-l-lysine to a desired thickness, where Poly-l-lysine is used; and
modifying the Agarose to establish a desired amount of resilience where Agarose is used.

19. The method of claim 17, wherein providing a biologically compatible material layer comprises at least one of:
establishing a thicknesses of the biologically compatible material layer to be less than a wavelength of light divided by two times a numerical aperture ($\lambda/(2*NA)$) of collection optics of a corresponding spectroscopic system;
establishing a thickness of the biologically compatible material layer having a Raman cross-section smaller than a predetermined Raman cross-section selected according to the spectroscopic evaluation, where the Raman cross-section is proportional to a function of a wavelength of incident photons produced by the corresponding Raman spectroscopic system;
providing a biologically compatible material layer that is free of symmetrical molecular moieties (such as tryptophan) and/or is further free of unsaturated chemical bonds; or providing a biologically compatible material layer that does not selectively bind calcium ions, sodium ions, and/or potassium ions and does not significantly suppress ion diffusion in condensed phase solutions.

20. The method of claim 17, wherein providing a biologically compatible material layer comprises at least one of:
providing a non-selective binding material that promotes adhesion; or
supporting biological culturing of the biological target collected upon the substrate.

* * * * *